United States Patent
Destache et al.

(10) Patent No.: US 10,179,134 B2
(45) Date of Patent: Jan. 15, 2019

(54) POLYMERIC NANOPARTICLES IN A THERMOSENSITIVE GEL FOR COITAL-INDEPENDENT VAGINAL PROPHYLAXIS OF HIV

(71) Applicant: Creighton University, Omaha, NE (US)

(72) Inventors: Chris Destache, Omaha, NE (US); Abhijit Date, Baltimore, MD (US); Annemarie Shibata, Omaha, NE (US)

(73) Assignee: Creighton University, Omaha, NE (US)

( * ) Notice: Subject to any disclaimer, the term of this patent is extended or adjusted under 35 U.S.C. 154(b) by 0 days.

(21) Appl. No.: 14/422,747

(22) PCT Filed: Jul. 31, 2013

(86) PCT No.: PCT/US2013/052829
§ 371 (c)(1),
(2) Date: Feb. 20, 2015

(87) PCT Pub. No.: WO2014/039185
PCT Pub. Date: Mar. 13, 2014

(65) Prior Publication Data
US 2015/0190398 A1 Jul. 9, 2015

Related U.S. Application Data

(60) Provisional application No. 61/697,083, filed on Sep. 5, 2012.

(51) Int. Cl.
*A61K 9/00* (2006.01)
*A61K 9/06* (2006.01)
*A61K 9/51* (2006.01)
*A61K 47/10* (2017.01)
*A61K 31/513* (2006.01)
*A61K 31/536* (2006.01)

(52) U.S. Cl.
CPC .......... *A61K 31/536* (2013.01); *A61K 9/0036* (2013.01); *A61K 9/06* (2013.01); *A61K 9/5153* (2013.01); *A61K 31/513* (2013.01); *A61K 47/10* (2013.01)

(58) Field of Classification Search
None
See application file for complete search history.

(56) References Cited

U.S. PATENT DOCUMENTS

2010/0273733 A1 10/2010 Fabunan

OTHER PUBLICATIONS

Arts et al. Cold Spring Harb Perspect Med, 2012, 2(4), pp. 1-23.*
HIV Transmission, Centers for Disease Control and Prevention, accessed on line on Jun. 21, 2016 at www.cdc.gov/hiv/basics/transmission.html.*

(Continued)

*Primary Examiner* — Carlos A Azpuru
*Assistant Examiner* — Casey S Hagopian
(74) *Attorney, Agent, or Firm* — Mallory M. Henninger; Advent, LLP

(57) ABSTRACT

An antiretroviral composition that gels upon heating and can be administered prophylactically prior to exposure to a retrovirus following sexual intercourse, and methods of using the same.

6 Claims, 21 Drawing Sheets

(56) References Cited

OTHER PUBLICATIONS

Sharma et al. "Pure drug and polymer based nanotechnologies for the improved solubility, stability, bioavailability and targeting of anti-HIV drugs", Advanced Drug Delivery Reviews, 62 (2010) 491-502.*

Aka-Any-Grah et al. "Formulation of mucoadhesive vaginal hydrogels insensitive to dilution with vaginal fluids", European Journal of Pharmaceutics and Biopharmaceutics, 76 (2010) 296-303.*

Armelle Aka-Any-Grah, Kawthar Bouchemal, Armand Koffi, Florence Agnely, Min Zhang, Madeleine Djabourov, Gilles Ponchel; Formulation of mucoadhesive vaginal hydrogels insensitive to dilution with vaginal fluids; European Journal of Pharmaceutics and Biopharmaceutics; 2010; vol. 76; pp. 296-303.

Puneet Sharma, Sanjay Garg; Pure drug and polymer based nanotechnologies for the improved solubility, stability, bioavailability and targeting of anti-HIV drugs; Advanced Drug Delivery Reviews; 2010; vol. 62; pp. 491-502.

Valence M. K. Ndesendo, Viness Pillay, Yahya E. Choonara, Eckhart Buchmann, David N. Bayever, and Leith C. R. Meyer; A Review of Current Intravaginal Drug Delivery Approaches Employed for the Prophylaxis of HIV/AIDS and Prevention of Sexually Transmitted Infections; AAPS PharmSciTech; Jun. 2008; vol. 9, No. 2; pp. 505-520.

Abhijit A. Date, Annemarie Shibata, Michael Goede, Bridget Sanford, Krista La Bruzzo, Michel Belshan, Christopher J. Destache; Development and evaluation of a thermosensitive vaginal gel containing raltegravir + efavirenz loaded nanoparticles for HIV prophylaxis; Antiviral Research; 2012; vol. 96; pp. 430-436.

* cited by examiner

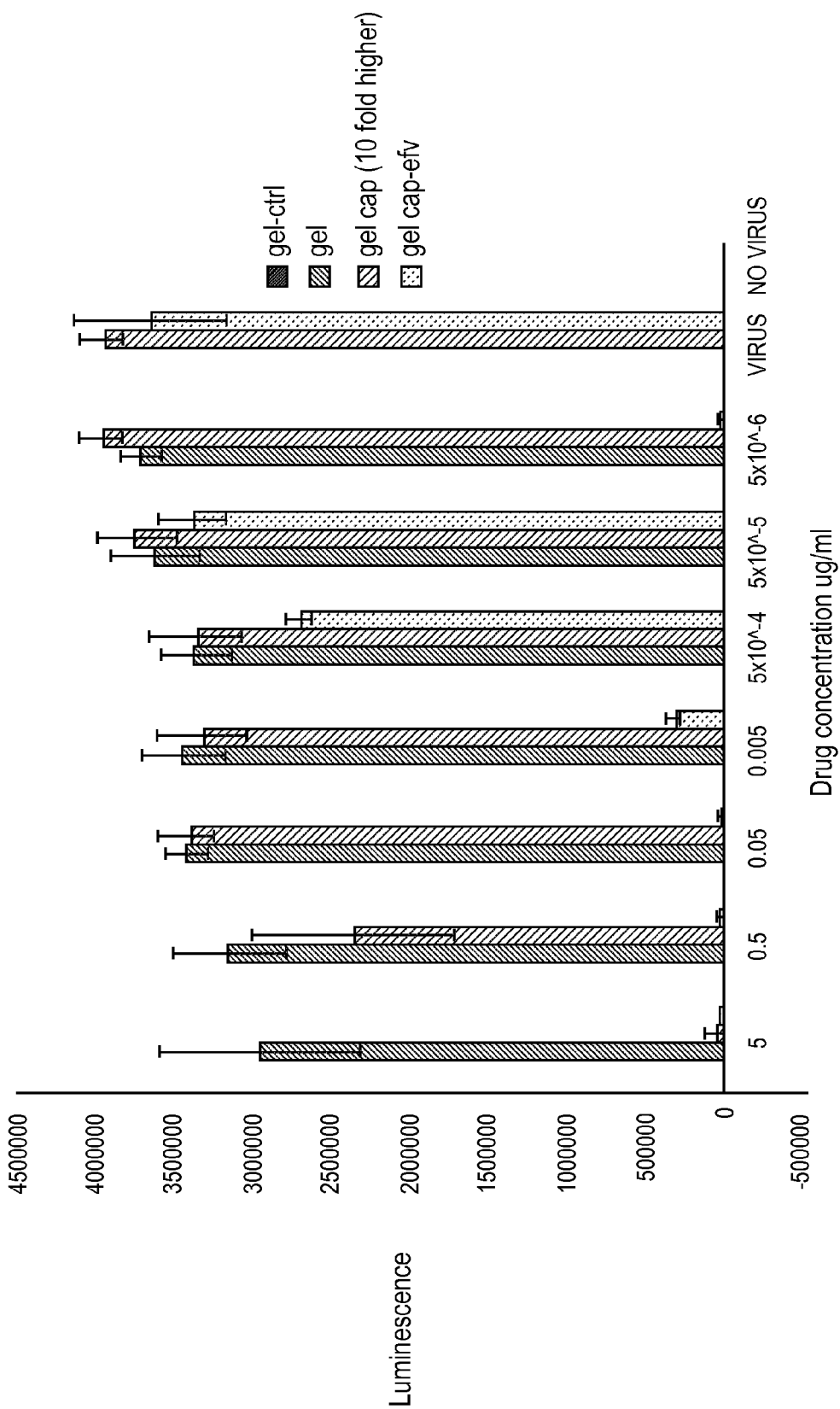

POLYMERIC NANOPARTICLES IN A THERMOSENSITIVE GEL FOR COITAL-INDEPENDENT VAGINAL PROPHYLAXIS OF HIV

GOVERNMENTAL RIGHTS

This invention was made with government support under NIH R56 AI095115 and NIH R01 AI080348 awarded by the National Institute of Health. The government has certain rights in the invention.

BACKGROUND

Prevention of HIV-1 infection to reduce the number of newly infected patients is an international priority. Various modalities such as male circumcision, prophylactic HIV vaccines, vaginal microbicides and oral pre-exposure prophylaxis have been explored to prevent sexual contraction of HIV. Prevention of HIV infection by using anti-viral agents as vaginal microbicides has received more attention in recent years.

Worldwide, nearly half of all individuals living with HIV are now women, who acquire the virus largely by heterosexual exposure. Many women, because of limited economic options and gender inequality, cannot reliably negotiate sexual encounters, leaving them vulnerable to unwanted pregnancy and sexually transmitted infections (STIs), including HIV. In the absence of an effective vaccine, topical microbicide formulations, which are applied vaginally or rectally, represent an attractive solution to stop HIV transmission. However, clinical trials focusing on vaginal prophylaxis of HIV using topical microbicides have shown mixed results. Several topical microbicides such as BufferGel™, PRO 2000, and Carraguard™ have failed to show efficacy in clinical trials whereas coitally-dependent administration of 1% tenofovir gel has shown success. Conversely, the VOICE trial employing a coitus-independent, once daily administration of 1% tenofovir gel was halted due to lack of efficacy. The VOICE trial setback has prompted investigators to examine alternatives. Therefore, there is a need for new anti-viral gels that provide sustained delivery of anti-viral therapy for the prevention of sexual HIV transmission but can be used coitally-independent.

BRIEF DESCRIPTION OF THE FIGURES

FIGS. 2 A and C show cell viability at 24 h and FIGS. 2 B and D show cell viability at 48 h.

FIG. 9 shows graphs depicting anti-HIV activity of a thermosensitive gel containing CAP-NP or CAP-EFV-NP. Briefly, TZM-bl cells were pretreated with either gel-control (gel-ctrl), gel alone (gel), gel containing CAP-NP (gel-cap (10-fold higher)), and gel containing CAP-EFV-NP (gel cap-efv), and then inoculated with HIV-$1_{NL4-3}$. After incubating the cells for a defined period of time, cells were lysed, a luciferase substrate (Bright-Glo) was added, and luminescence was expressed as relative luminescence units.

DETAILED DESCRIPTION

Figure 1:
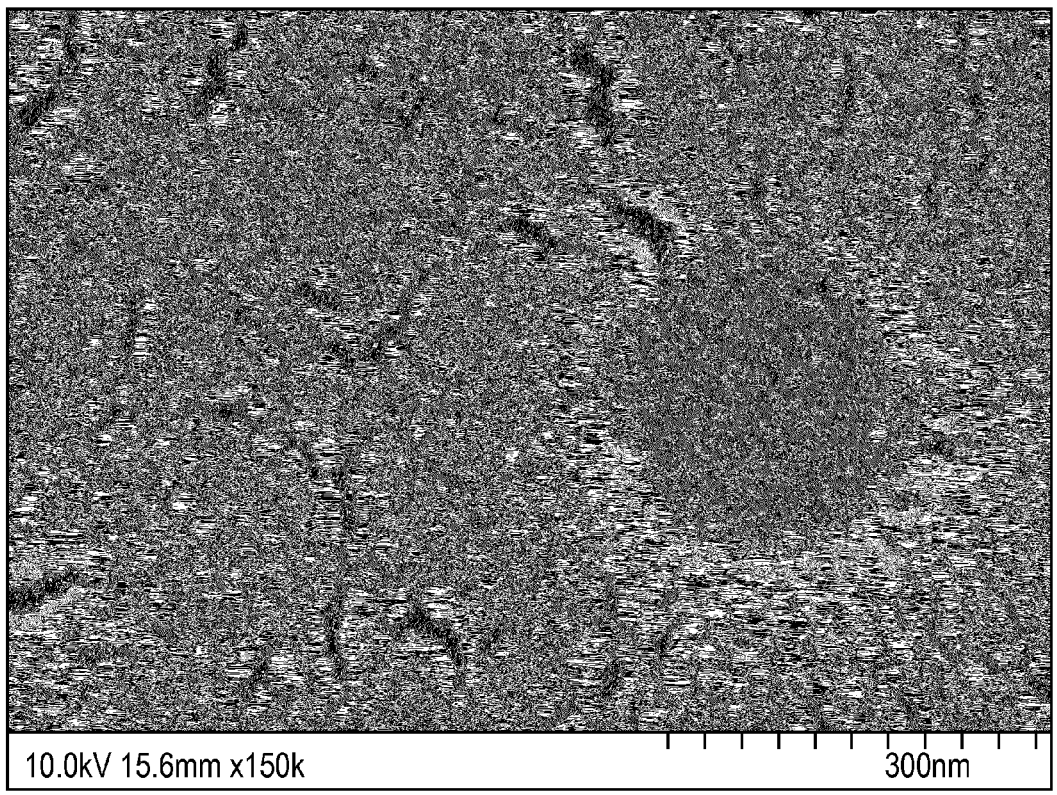
FIG. 1 depicts a scanning electron micrograph (SEM) image of the raltegravir+efavirenz loaded PLGA nanoparticles.
Figure 2A:
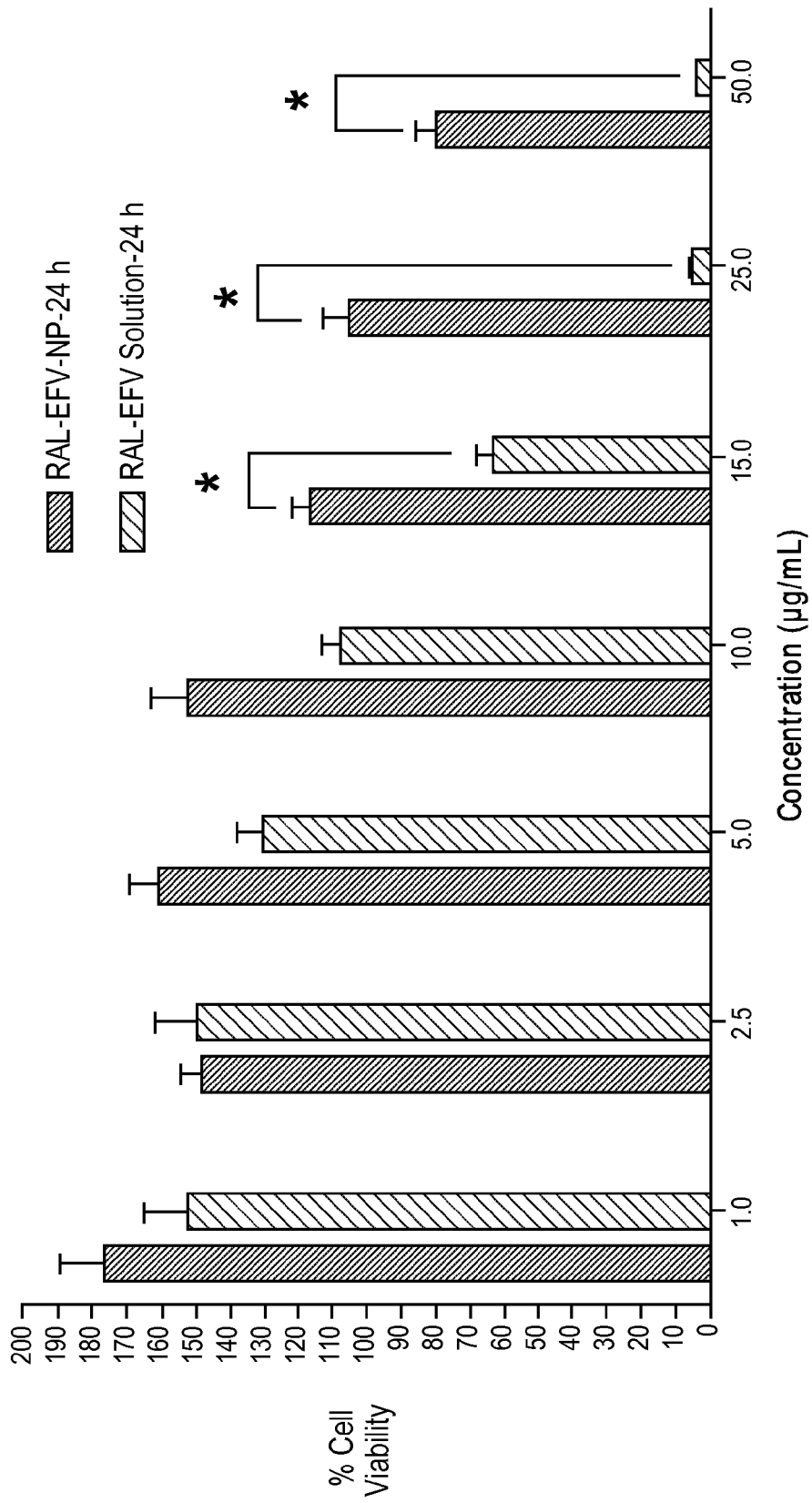
FIG. 2 graphically depicts the cytotoxicity of RAL-EFV-NP and RAL-EFV solution to H9 cells (A and B) and HeLa cells (C and D) in vitro.
Figure 2B:
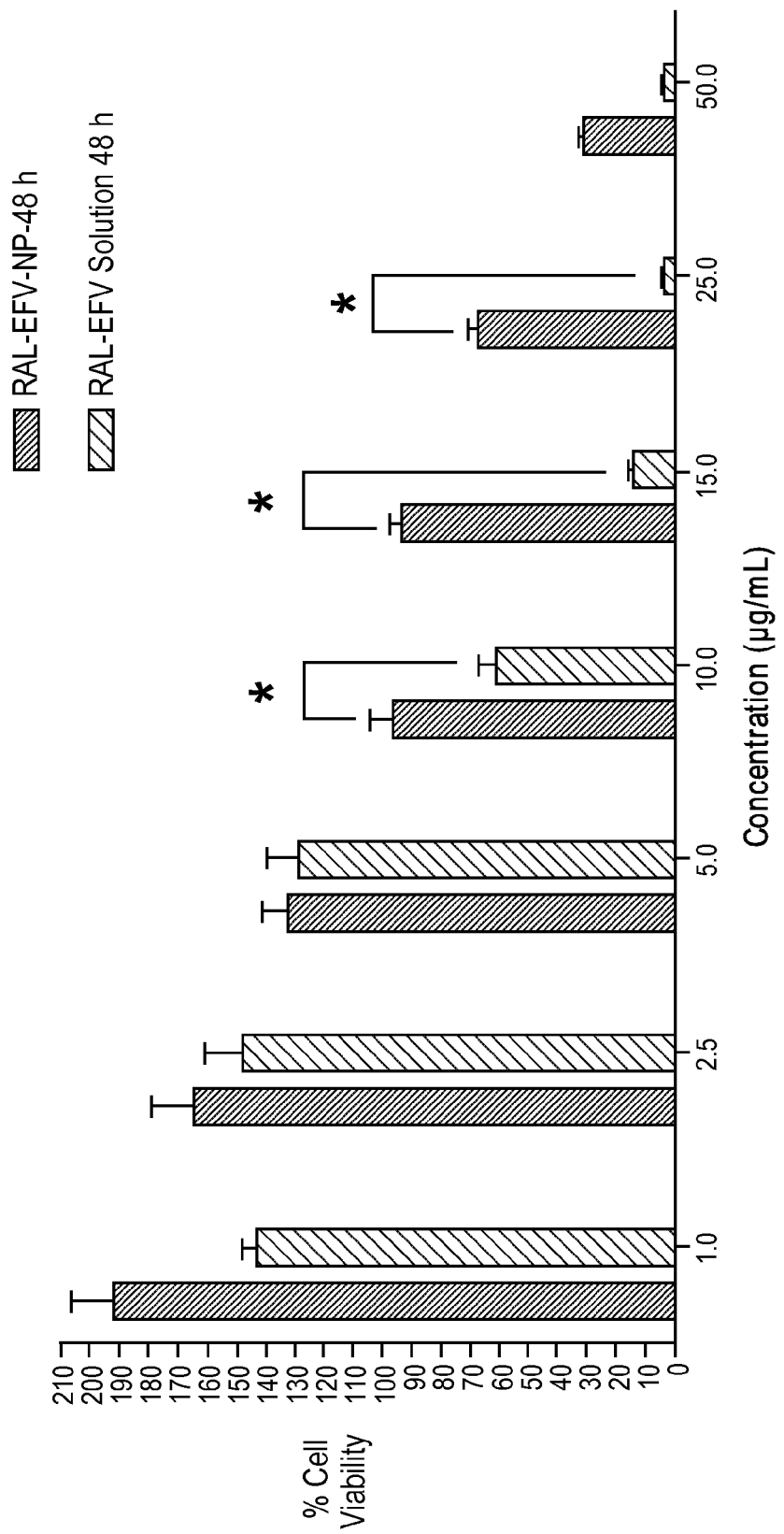
Figure 2C:
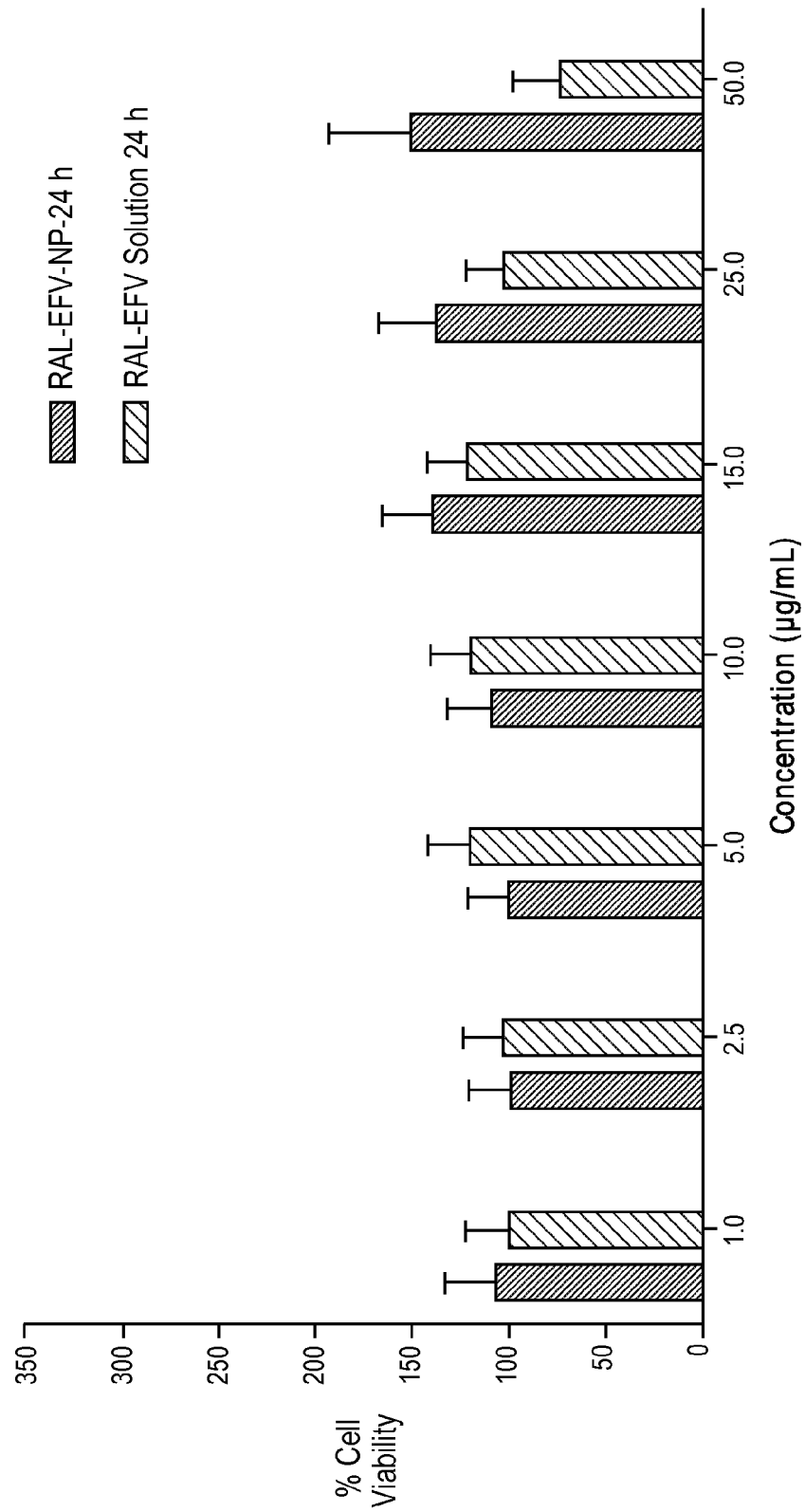
Figure 2D:
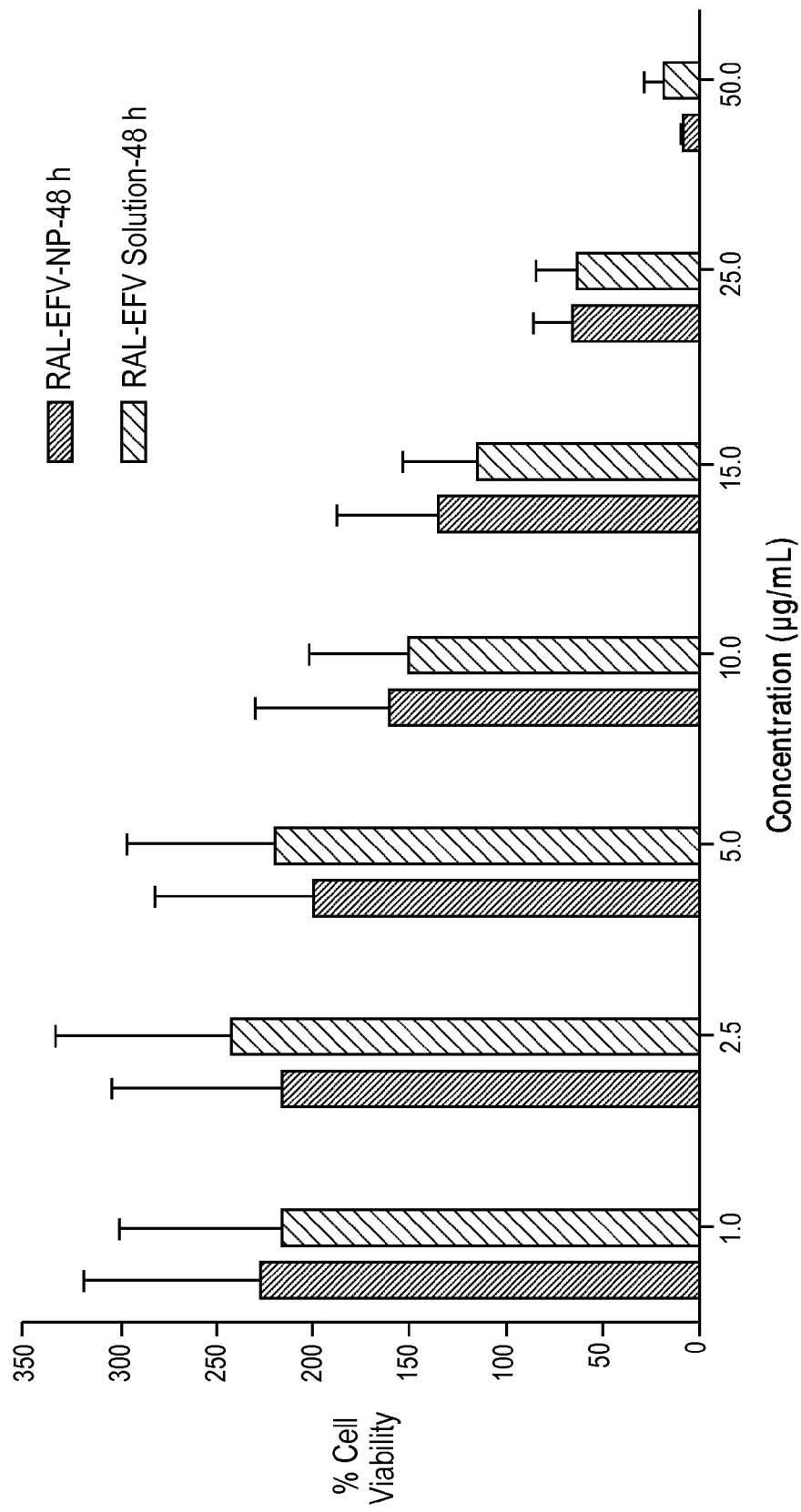

The disclosure provides an ARV composition that gels upon heating and can be administered prophylactically. It has been discovered that incorporation of one or more antiretroviral (ARV) drugs with polymeric nanoparticles results in sustained intracellular release of the ARV drugs. Furthermore, ARV intracellular concentrations were consistent with levels that can offer protection from HIV-1 infection for multiple days. Finally, successful incorporation of the ARV nanoparticles into a thermosensitive gel provides a suitable means for vaginal or rectal delivery. The ARV composition that gels upon heating and can be administered prophylactically, its method of use, and other components are described in further detail below.

(a) Thermosensitive Gel

According to the disclosure, the composition gels upon heating. As used herein, the term "gels" can refer to any process by which a composition changes from a solution into a gel (i.e. undergoes a sol-gel transition), and the term "thermosensitive gel" can refer to a polymeric system that undergoes a sol-gel transition due to temperature. Generally speaking, the composition is a thermosensitive gel that is a solution at room temperature but forms a gel once delivered inside the body. For example, the gel can be a citric acid based aqueous substance with a pH of about 4.5 to be compatible with a female reproductive track pH. One skilled in the art will appreciate that "room temperature" will vary depending on the local climate. In an exemplary embodiment, the thermosensitive gel remains a liquid in subtropical and tropical countries or in the zone IV as classified by the guidelines from the International Conference on Harmonisation of Technical Requirements for Registration of Pharmaceuticals for Human Use. For example, the thermogelation temperature can be between 30-35° C. In some embodiments, the thermogelation temperature can be about 30.0° C., 30.1° C., 30.2° C., 30.3° C., 30.4° C., 30.5° C., 30.6° C., 30.7° C., 30.8° C., 30.9° C., 31° C., 31.1° C., 31.2° C., 31.3° C., 31.4° C., 31.5° C., 31.6° C., 31.7° C., 31.8° C., 31.9° C., 32° C., 32.1° C., 32.2° C., 32.3° C., 32.4° C., 32.5° C., 32.6° C., 32.7° C., 32.8° C., 32.9° C., 33° C., 33.1° C., 33.2° C., 33.3° C., 33.4° C., 33.5° C., 33.6° C., 33.7° C., 33.8° C., 33.9° C., 34° C., 34.1° C., 34.2° C., 34.3° C., 34.4° C., 34.5° C., 34.6° C., 34.7° C., 34.8° C., 34.9° C., or 35° C. In other embodiments, the thermogelation temperature can be about 30 to about 33° C.

A variety of polymers undergoes sol-gel transitions due to temperature and can be used. In some embodiments, the thermosensitive polymer is synthetic or naturally derived. In other embodiments, the thermosensitive polymer can also have mucoadhesive or bioadhesive properties. In still other embodiments, the thermosensitive polymer does not have mucoadhesive or bioadhesive properties. In yet other embodiments, thermosensitive polymers are combined with mucoadhesive polymers. The thermosensitive polymer and its gel can be biocompatible when used for pharmaceutical applications. As used herein, "biocompatible" means the polymer does not typically induce significant inflammation and/or acute rejection of the polymer by the immune system when introduced into a living subject. Non-limiting examples of suitable thermosensitive polymers can include chitosan-based copolymers, Nisopropylacrylamide copolymers, poly(ethylene oxide)/poly(propylene oxide) block copolymers, poly(ethylene glycol)/poly(D,L-lactide-co-glycolide) block copolymers, and poloxamers. Poloxamers are non ionic triblock copolymers composed of a central hydrophobic chain of polyoxypropylene (poly(propylene oxide)) flanked by two hydrophilic chains of polyoxyethylene (poly(ethylene oxide)). Poloxamers are also known by the trade name PLURONIC® and Kolliphor. In some embodiments, the polymeric system can be comprised of a PLURONIC® or a mix of Pluronics. In a other embodiments, the polymeric system can be comprised of PLURONIC® F127 and Pluronic F68. The ratio of PLURONIC® F127 to PLURONIC® F68 can vary. In some embodiments, the ratio of PLURONIC® F127 to PLURONIC® F68 (% weight/volume) is between about 20%: 1% to about 18%:1%. In other embodiments the ratio of PLURONIC® F127 to PLURONIC® F68 (% weight/volume) is between about 20%:2% to about 18%:2%. In still other embodiments, the ratio of PLURONIC® F127 to PLURONIC® F68 (% weight/volume) is 20%:1%.

Methods of developing a thermosensitive gel can include mixing known quantities of one or more thermosensitive polymers in solution, and determining the thermogelation point of the gel and dynamic viscosity. Pharmaceutical formulations and other compositions can be incorporated by solution mixing. Methods of developing a thermosensitive gel are described in more detail in the Examples.

(b) Administered Prophylactically

The composition can be administered prophylactically. Prophylactic use prior to exposure (pre-exposure prophylaxis) is a prevention method in which people who are not virally infected take medication to reduce their risk of infection in the event of exposure to the virus following sexual intercourse. However, a prophylaxis can also be effective shortly before or shortly after exposure to the virus following sexual intercourse. In some embodiments, the composition is administered peri-coital. In other embodiments, the composition is administered post-coital. In still other embodiments, the composition is administered pre-coital.

The amount of time that can elapse between administration of the composition and viral exposure can and will vary depending on variables such as the ARV drug or combination of ARV drugs in the composition, as well as the amount (or dose) of the ARV drug or combination of ARV drugs. Coitally-dependent gels require insertion within a brief window of time before sexual intercourse. The composition is developed as a coitally-independent gel. In some embodiments, the composition can be administered about 12 hours prior to exposure. In other embodiments, the composition can be administered about 1 day, about 2 days, about 3 days, about 4 days, about 5 days, about 6 days, about 7 days, about 8 days, about 9 days, about 10 days, about 11 days, about 12 days, about 13 days, or about 14 days prior to exposure. In still other embodiments, the composition can be administered up to and including about 1 week prior to exposure.

The composition can be administered vaginally or rectally. The composition can be provided as dry powder to be reconstituted, a liquid or as a gel. In one method of administration, the composition can be maintained at a temperature of less than the thermogelation temperature to keep it in a liquid state, and injected into the vagina or the anus, where it forms a gel when at the temperature of the human body. In another method of administration, the composition can be brought to a temperature on or about its thermogelation temperature to form a gel, and then injected as a gel into the vagina or the anus. A syringe, or any other device known in the art, can be used for injection. If to be injected as a gel, the composition can be warmed in the syringe to form a gel, and injected from the syringe as a gel to the affected site. Alternatively the composition can be in the gel state when it is loaded into the syringe. In still another method of administration, the composition can be brought to a temperature on or about its thermogelation temperature to form a gel in the presence of a device that can be inserted into the vagina (e.g. intravaginal rings or diaphragms), such that the gel forms on the device. Alternatively, the composition can also be formulated in rectal compositions such as suppositories or retention enema, using, e.g., suppository bases such as cocoa butter or other glycerides.

(c) Nanoparticle

The composition comprises a nanoparticle, the nanoparticle further comprising a polymer and at least one ARV drug. The term "particle" and "nanoparticle", or the abbreviation "NP" for nanoparticle, as used herein, can refer to particles between I0 and I000 nanometers (nm) in diameter and are used interchangeably. In these embodiments, the ARV drug is incorporated into a suitable particle to aid in the delivery of the drug to target cells, to increase the stability of the composition, to minimize potential toxicity of the composition, or a combination thereof. A variety of nanoparticles are suitable for delivering an ARV drug.

The size of the particle can influence the ability of the particle to rapidly penetrate through vaginal mucus. For instance, the nanoparticle can have small particle size for successful vaginal delivery. In some embodiments, the diameter of a nanoparticle can be at least 10 nm, at least 20 nm, at least 30 nm, at least 40 nm, at least 50, at least 60 nm, at least 70 nm, at least 80 nm, at least 90 nm, or at least 100 nm. In other embodiments, the particle can be greater than about 100 nm in diameter. For example, the diameter of the nanoparticle can be at least 110 nm, at least 120 nm, at least 130 nm, at least 140 nm, at least 150 nm, at least 160 nm at least 170 nm, at least 180 nm, at least 190 nm, or at least 200 nm. In an exemplary embodiment, the nanoparticle can be less than 220 nm in diameter. In still other embodiments, the particle can be less than about 100 nm in diameter.

In some embodiments, the particle can have a surface charge that is positive or negative. For example, in certain embodiments where a nanoparticle has a negative surface charge, the surface charge can be at least −40 millivolts (mV), at least −35 mV, at least −30 mV, at least −25 mV, at least −20 mV, no greater than −10 mV, no greater than −15 mV, no greater than −20 mV, no greater than −25 mV, or any combination thereof. In an exemplary embodiment, a nanoparticle can have a negative surface charge of at least −30 mV to no greater than −10 mV. In other embodiments wherein a nanoparticle has a positive surface charge, the surface charge can be at least 2 millivolts (mV), at least 15 mV, at least 20 mV, at least 25 mV, or at least 30 mV, no greater than 40 mV, no greater than 35 mV, no greater than 30 mV, no greater than 25 mV, or any combination thereof.

In some embodiments, the particle can have an osmolarity of less than about 1000 mOsm/kg. In other embodiments, the particle can have an osmolarity less than about 500 mOsm/kg. For example, the particle can have an osmolarity of about 50 mOsm/kg, about 100 mOsm/kg, about 150 mOsm/kg, about 200 mOsm/kg, about 250 mOsm/kg, about 300 mOsm/kg, about 350 mOsm/kg, about 400 mOsm/kg, about 410 mOsm/kg, about 420 mOsm/kg, about 430 mOsm/kg, about 440 mOsm/kg, about 450 mOsm/kg, about 460 mOsm/kg, about 470 mOsm/kg, about 480 mOsm/kg, or about 490 mOsm/kg. In another embodiment, the particle can have an osmolarity of at least 500 mOsm/kg to no greater than 1000 mOsm/kg. For example, the particle can have an osmolarity of about 500 mOsm/kg, about 600 mOsm/kg, about 700 mOsm/kg, about 800 mOsm/kg, about 900 mOsm/kg, or about 1000 mOsm/kg.

(i) Biodegradable Polymer

Each particle can have one or more biodegradable polymers. An example of such a particle comprising a biodegradable polymer and methods of making the particle is disclosed in patent application publication number US 2011/0236437, which is incorporated herein by reference in its entirety. Briefly, a "polymer," as used herein, is given its ordinary meaning as used in the art, i.e., a molecular structure including one or more repeat units (monomers), connected by covalent bonds. The repeat units can all be identical, or in some cases, there can be more than one type of repeat unit present within the polymer. A polymer can be natural (e.g., biologically derived) or unnatural (e.g., synthetically derived). Polymers can be homopolymers or copolymers including two or more monomers. In teens of sequence, copolymers can be random, block, or can include a combination of random and block sequences. If more than one type of repeat unit is present within the polymer, then the polymer is said to be a "copolymer." It is to be understood that in any aspect employing a polymer, the polymer can be a copolymer.

A biodegradable polymer is able to degrade, chemically and/or biologically, within a physiological environment, such as within the body. For instance, the polymer can be one that hydrolyzes spontaneously upon exposure to water (e.g., within a subject), or degrades upon exposure to heat (e.g., at temperatures of 42° C.). Degradation of a polymer can occur at varying rates, depending on the polymer or copolymer used. For example, the half-life of the polymer (the time at which 50% of the polymer is degraded into monomers and/or other nonpolymeric moieties) can be on the order of days or weeks, depending on the polymer. The polymers can be biologically degraded, e.g., by enzymatic activity or cellular machinery. In some cases, the polymers can be broken down into monomers and/or other nonpolymeric moieties that cells can either reuse or dispose of without significant toxic effect on the cells (for example, polylactide can be hydrolyzed to form lactic acid, polyglycolide can be hydrolyzed to form glycolic acid, etc.).

In some embodiments, the biodegradable polymer can be a natural polymer. In other embodiments, biodegradable the polymer can be a synthetic polymer. Non-limited examples of natural and synthetic polymers useful in the preparation of biodegradable particles can include carbohydrates such as alginate, cellulose, polyhydroxyalkanoates, polyamides, polyphosphazenes, polypropylfumarates, polyethers, polyacetals, polycyanoacrylates, biodegradable polyurethanes, polycarbonates, polyanhydrides, polyhydroxyacids. poly(ortho esters), and polyesters. Non-limiting examples of polyesters can include polymers including, but not limited to, polycaprolactone, or copolymers including, but not limited to, lactic acid and glycolic acid units, such as poly(lactic acid-coglycolic acid) and poly(lactide-co-glycolide), collectively referred to herein as "PLGA"; and homopolymers including glycolic acid units, and lactic acid units, such as poly-L-lactic acid, poly-D-lactic acid, poly-D,L-lactic acid, poly-L-lactide, poly-D-lactide, and poly-D,L-lactide. In some embodiments, the polymer can be PLGA. In another embodiment, the polymer can be polycaprolactone. In yet another embodiment, the polymer can be cellulose acetate phthalate.

(ii) ARV Drug

In addition to the biodegradable polymer, each particle can comprise one or more antiretroviral (ARV) drugs. ARV drugs are broadly classified by the phase of the retrovirus life-cycle the drug inhibits. Classes of ARV drugs can include entry inhibitors, CCR5 receptor antagonists, nucleoside reverse transcriptase inhibitors, nucleotide reverse transcriptase inhibitors, non-nucleoside reverse transcriptase inhibitors, protease inhibitors, integrase inhibitors, and maturation inhibitors. Conditions which can be inhibited, prevented or treated with an ARV drug, and thus a composition of the present invention, include all conditions associated with HIV, including, but not limited to HIV-1 and HIV-2 infections, and other pathogenic retroviral infections, including AIDS. Management of HIV/AIDS can rely on the use of two or more ARV drugs taken in combination. In some embodiments of the invention, ARV drugs can inhibit a retrovirus. In other embodiments, the retrovirus is HIV. In alternative embodiments, ARV drugs can inhibit other viruses. For instance, a 1% tenofivir vaginal gel has been shown to inhibit herpes simplex virus-2 transmission. The disclosure is not limited to inhibiting retroviruses in general, or HIV specifically.

The ARV drugs can be selected from same or different class of ARV drugs. Non-limiting examples of ARV drug classes can include nucleoside reverse transcriptase inhibitors, nucleotide reverse transcriptase inhibitors, non-nucleoside reverse transcriptase inhibitors, protease inhibitors, integrase inhibitors, fusion inhibitors, entry inhibitors (CCR5 co-receptor antagonists) and maturation inhibitors. Non-limiting examples of nucleoside reverse transcriptase inhibitors can include zidovudine, didanosine, stavudine, zalcitabine, abacivir, emtricitabine, and lamivudine. Non-limiting examples of nucleotide reverse transcriptase inhibitors can include tenofovir. Non-limiting examples of non-nucleoside reverse transcriptase inhibitors can include efavirenz (EFV), rilpivirine, etravirine, nevirapine, and delaviradine. Non-limiting examples of protease inhibitors can include HIV protease inhibitors, such as atazanavir, darunavir, indinavir, amprenavir, tipranavir, ritonavir, saquinavir, lopinavir, and nelfinavir. Non-limiting examples of integrase inhibitors can include raltegravir (RAL), elvitegravir dolutegravir. A non-limiting example of a fusion inhibitor can include enfuviritide. A non-limiting example of an entry inhibitor can include mariviroc and cellulose acetate phthalate (CAP). Non-limiting examples of maturation inhibitors can include bevirimat.

In one embodiment, the particle comprises one ARV drug. In another embodiment, the particle comprises two ARV drugs. In yet another embodiment, the particle comprises three ARV drugs. In a different embodiment, the particle comprises four or more ARV drugs. In an exemplary embodiment, the particle comprises two or more ARV drugs selected from the same class. In an alternative embodiment, the particle comprises two or more ARV drugs selected from different classes. In yet another embodiment, the particle comprises two or more ARV drugs, wherein at least ARV drugs are selected from the same class and at least one ARV drug is selected from a different class. In yet another embodiment, the ARV drug is selected from the group consisting of efavirenz, raltegravir, cellulose acetate phthalate, tenofovir, emtricitabine, and combination thereof. Non-limiting examples of ARV drug combinations can include efavirenz plus cellulose acetate phthalate, efavirenz plus raltegravir, and tenofovir plus emtricitabine.

The ARV drug can be associated with the surface of, directly or indirectly conjugated to, encapsulated within, surrounded by, dissolved in, or dispersed throughout the polymeric matrix. The phrase "loaded into", "loaded onto", "incorporated into", or "included in" are used interchangeably to generally describe the association of the ARV drug with the particle without imparting any further meaning as to where or how the ARV drug is associated with the particle. The biochemical properties of the ARV drug can influence the method by which the ARV drug is included in the particle. For instance, a drug's hydrophilicity (as measured by its log P value at ph 7.4) can be used to guide such a decision, as the drug's hydrophilicity can influence the amount of drug that can be encapsulated within a particle. In some embodiments, a hydrophilic drug with a negative log P value at pH 7.4 can be encapsulated within the polymeric mixture, directly or indirectly conjugated to the polymeric mixture, or a combination thereof. In some embodiments, a lipophilic drug with a positive log P value at pH 7.4 can be encapsulated within the polymeric mixture, directly or indirectly conjugated to the polymeric mixture, or a combination thereof. In yet other embodiments, a combination of one or more lipophilic drugs and one or more hydrophilic drugs can be encapsulated within the polymeric mixture, directly or indirectly conjugated to the polymeric mixture, or a combination thereof.

Methods of including the ARV drug in the nanoparticle are described in more detail in the Examples. The amount of each agent present in a particle (entrapment efficiency) can be at least about 10% to as high as about 98% w/w). In some embodiments, the entrapment efficiency can be about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 98% (w/w). Similar to how the biochemical properties of an ARV drug can affect how the ARV drug is loaded into a particle, the biochemical properties can also affect the entrapment efficiency. In some embodiments, wherein the particle comprises two or more ARV drugs, the entrapment efficiency for each ARV drug can be similar. For example, the entrapment efficiency for each of the two or more ARV drugs can be at least about 10% but no greater than about 50% (w/w). In another example, the entrapment efficiency for each of the two or more ARV drugs can be at least about 50% but no greater than about 98% (w/w). In an alternative embodiment, wherein the particle comprises two or more ARV drugs, the entrapment efficiency for each ARV drug can be different. For example, the entrapment efficiency for at least one ARV drug can be at least about 10% but no greater than about 50% (w/w), and the entrapment efficiency for at least one other ARV drug can be at least about 50% but no greater than about 98% (w/w).

(iii) Additional Components

Particles can also optionally comprise polypeptides, small organic molecules, polysaccharides, polynucleotides, natural products, synthetic compounds, chemical compounds, or a combination thereof. In one embodiment, a particle can optionally comprise a substance that improves the mucous-penetrating ability of the particle. In another embodiment, a particle can optionally comprise a targeting molecule. A targeting molecule is able to bind a biological entity, such as a membrane or cell surface receptor. Suitable targeting molecules are known in the art. In an exemplary embodiment, a particle can optionally comprise a stabilizer. A non-limiting example of a stabilizer can include PLURONIC® F127.

(d) Methods of Use

Another aspect of the disclosure encompasses a method of prophylactically inhibiting a retroviral infection in an uninfected subject. The method comprises administering a composition of the invention to a subject. The subject can be a human or a nonhuman primate. In some embodiments, the subject can be a nonhuman primate. Nonlimiting examples of nonhuman primates can include macaques, marmosets, tamarins, spider monkeys, owl monkeys, vervet monkeys, squirrel monkeys, baboons, and chimpanzees.

In general, a prophylactic treatment comprises administration of a composition prior to exposure to the infectious agent (e.g. retrovirus). The timing of the administration and the overall period of time of treatment can and will vary, depending on the risk of exposure, for example. A subject may or may not be certain that exposure to a retrovirus will occur. In some cases, the human may not be aware that exposure will occur but can want to take preventative measures out of an abundance of caution. In other cases, the human can be aware that exposure to the retrovirus is likely, if not certain, though the timing of the exposure (i.e. when exposure to the retrovirus will occur) may not be known. In some methods of use, the composition is administered about once a day. In other methods of use, the composition is administered about once a week. In alternative methods of use, the composition is administered about 1 day, about 2 days, about 3 days, about 4 days, about 5 days, about 6 days, about 7 days, about 8 days, about 9 days, about 10 days, about 11 days, about 12 days, about 13 days, or about 14 days prior to exposure.

A further aspect of the disclosure encompasses inhibiting a retroviral infection in an uninfected subject. As used herein, the phrase "inhibiting a retroviral infection" can refer to preventing, blocking, stopping, disrupting, or reducing any viral activity that can lead to a retroviral infection. The effect on such activity can be determined by the assays described in the Example 3. Such activity can also be determined by plaque formation assays or any other assay to measure the cytopathic effect of a virus. Alternatively, such activity can be determined in a clinical study with human or nonhuman mammals.

In general, a method of the disclosure encompasses preventing a retroviral infection in an uninfected subject by prophylactically administering up to and including seven days prior to exposure to the retrovirus an antiretroviral composition that gels upon heating to a temperature of about 30° C. to about 33° C. The composition comprises a) a mixture of thermosensitive polymers and b) a nanoparticle comprising a biodegradable polymer and at least one ARV drug. In one embodiment, the mixture of thermosensitive polymers is a mixture of PLURONIC® F68 and PLURONIC® F127. In another variation, the antiretroviral drug is selected from a group consisting of raltegravir, efavirenz, and a combination thereof. In still another embodiment, the biodegradable polymer is selected from the group consisting of poly-lactide-co-glycolide or cellulose acetate phthalate.

EXAMPLES

The following examples illustrate various iterations of the invention.

Example 1

RAL-EFV-NP Preparation and Characterization

The PLGA nanoparticles containing RAL and EFV combination (RAL-EFV-NPs) had particle size of 81.8±6.4 nm, polydispersity index of 0.15±0.02 and the surface charge was −23.18±7.18 mV (n=3). The entrapment efficiency of the RAL and EFV in the nanoparticles averaged (+SEM) 55.5±5.61% and 98.2±1.2% respectively (n=3). Scanning electron microscopy showed the presence of sub-100 nm RAL-EFV-NP (FIG. 1) validating the results of dynamic light scattering. The osmolarity of RAL-EFV-NPs averaged 405.3±0.57 mOsm/kg due to presence of 1.5% v/v DMSO and 1% v/v N-methylpyrrolidone.

Example 2

In vitro Cytotoxicity Studies

Figure 11:
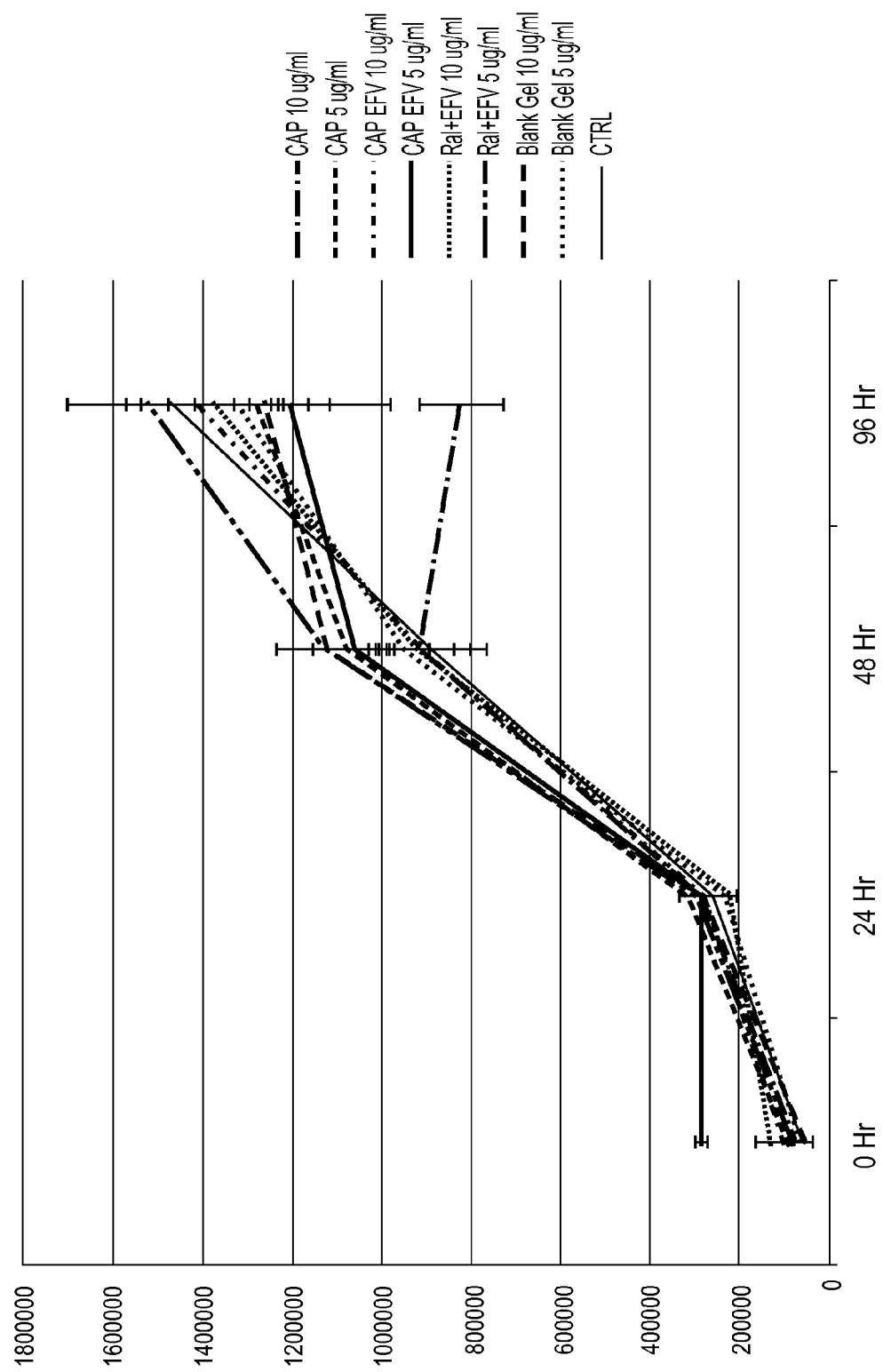
FIG. 11 shows a line graph depicting cytotoxicity of gel containing CAP-NP (CAP), gel containing CAP-EFV-NP (CAP EFV), gel containing RAL-EFV solution (Ral+EFV) and a gel control (Blank Gel without any nanoparticles) to HeLa cells over 96 hours in vitro. The control (CTRL) are control cells without anything added to the wells (e.g. no nanoparticles or gel). Relative luminescence is graphed on the y-axis, corresponding to HeLa cell viability.
Figure 12A:
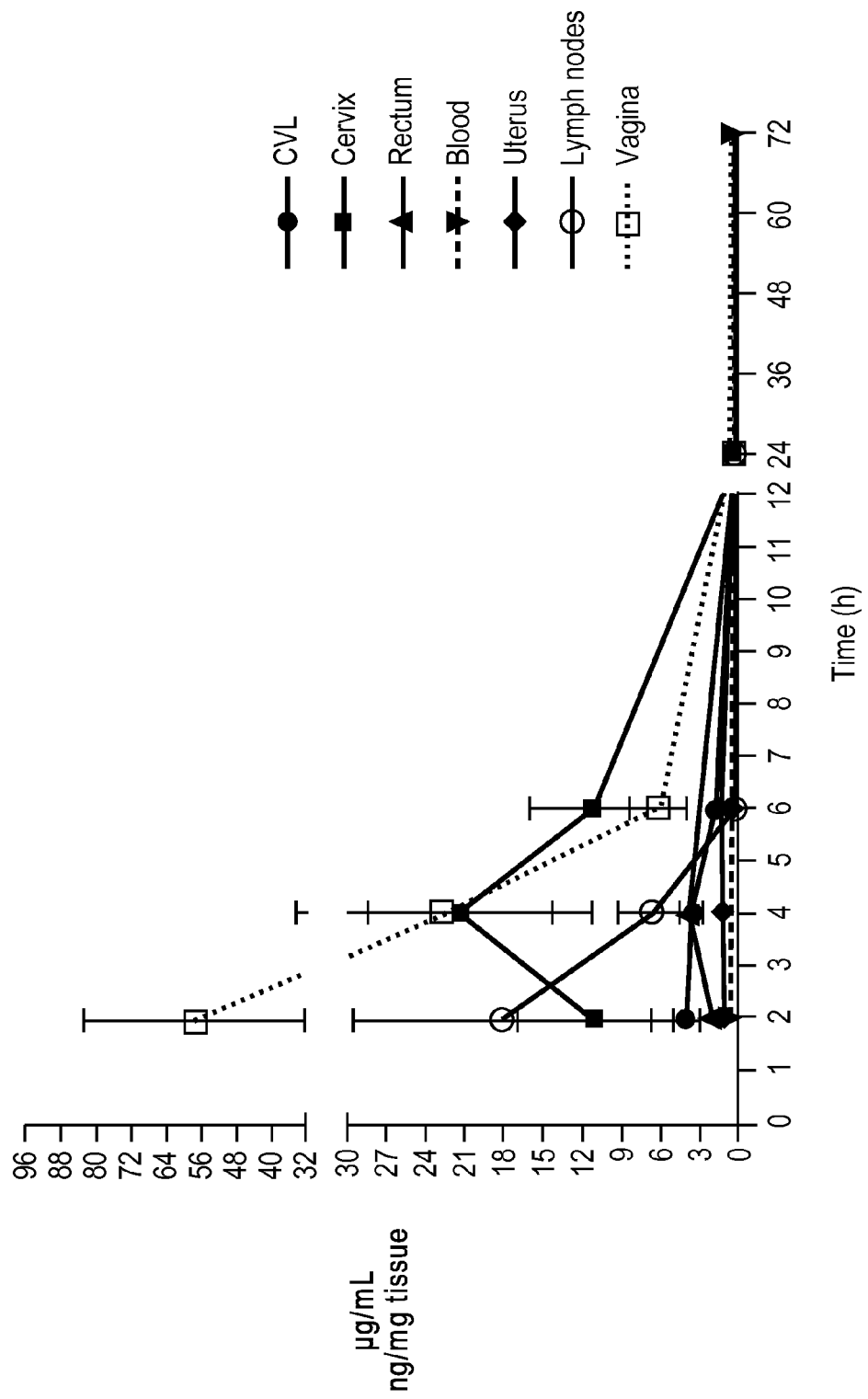
FIG. 12 shows a line graph depicting raltegravir (A) and efavirenz (B) levels in tissue sampled from different parts of the female mouse reproductive tract. Here, 30 uL of gel containing RAL+EFV NPs in gel were intravaginally instilled into female mice. At specific times (plotted on the X-axis), the mice were euthanized and the tissue harvested. Tissue was homogenized in acetonitrile and an aliquot of the supernatants were analyzed by HPLC for raltegravir or efavirenz. The Y-axis is depicted as ng/mg tissue weight. Additionally, at specific times, 50 uL of PBS was instilled into the vaginal tract and collected as cervicovaginal lavage to determine amounts of drugs from NPs were remaining in the vaginal tracts of the mice. The cervicovaginal lavage was measured in ug/mL (1000 fold higher than the tissue levels).
Figure 12B:
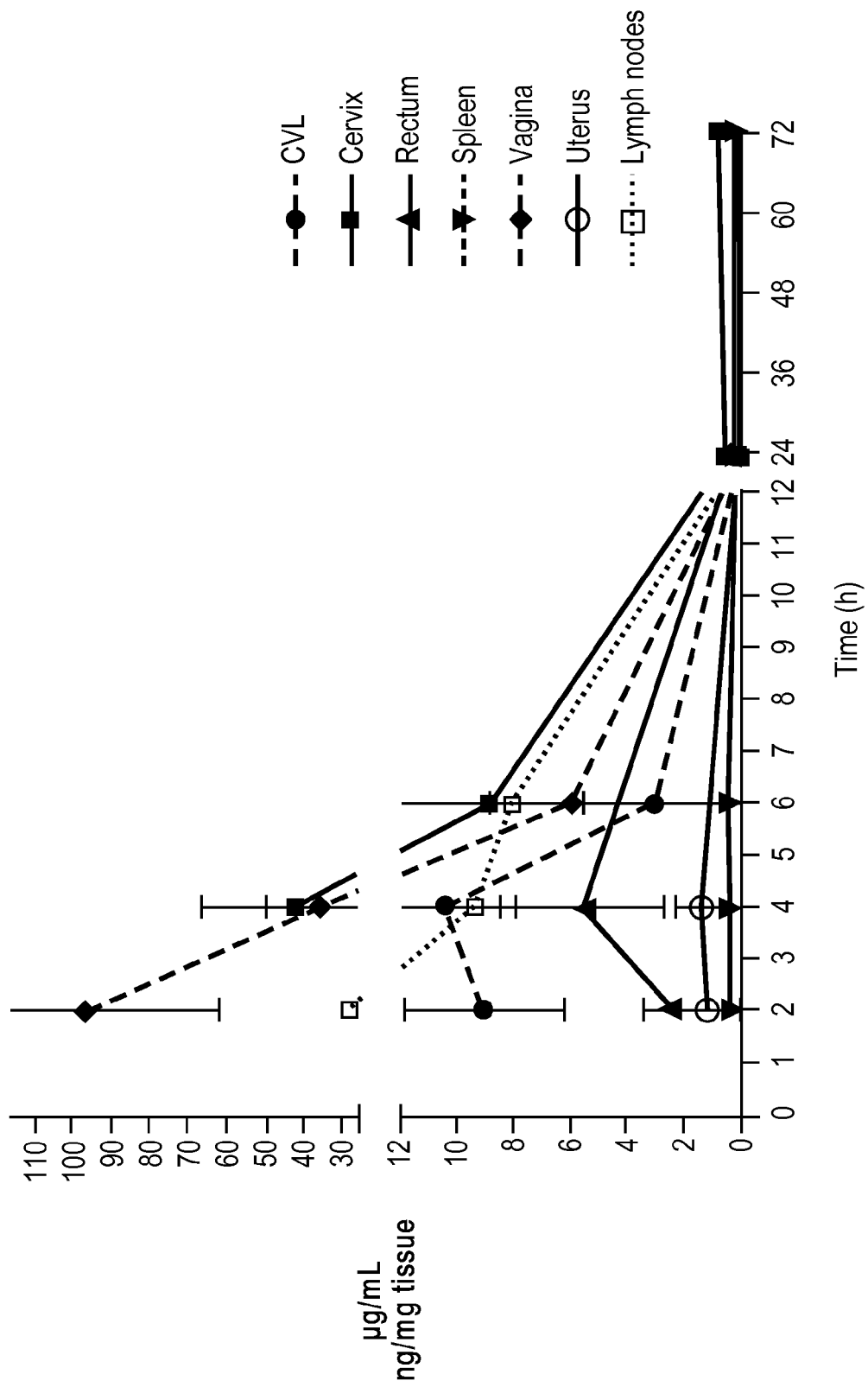
Figure 13:
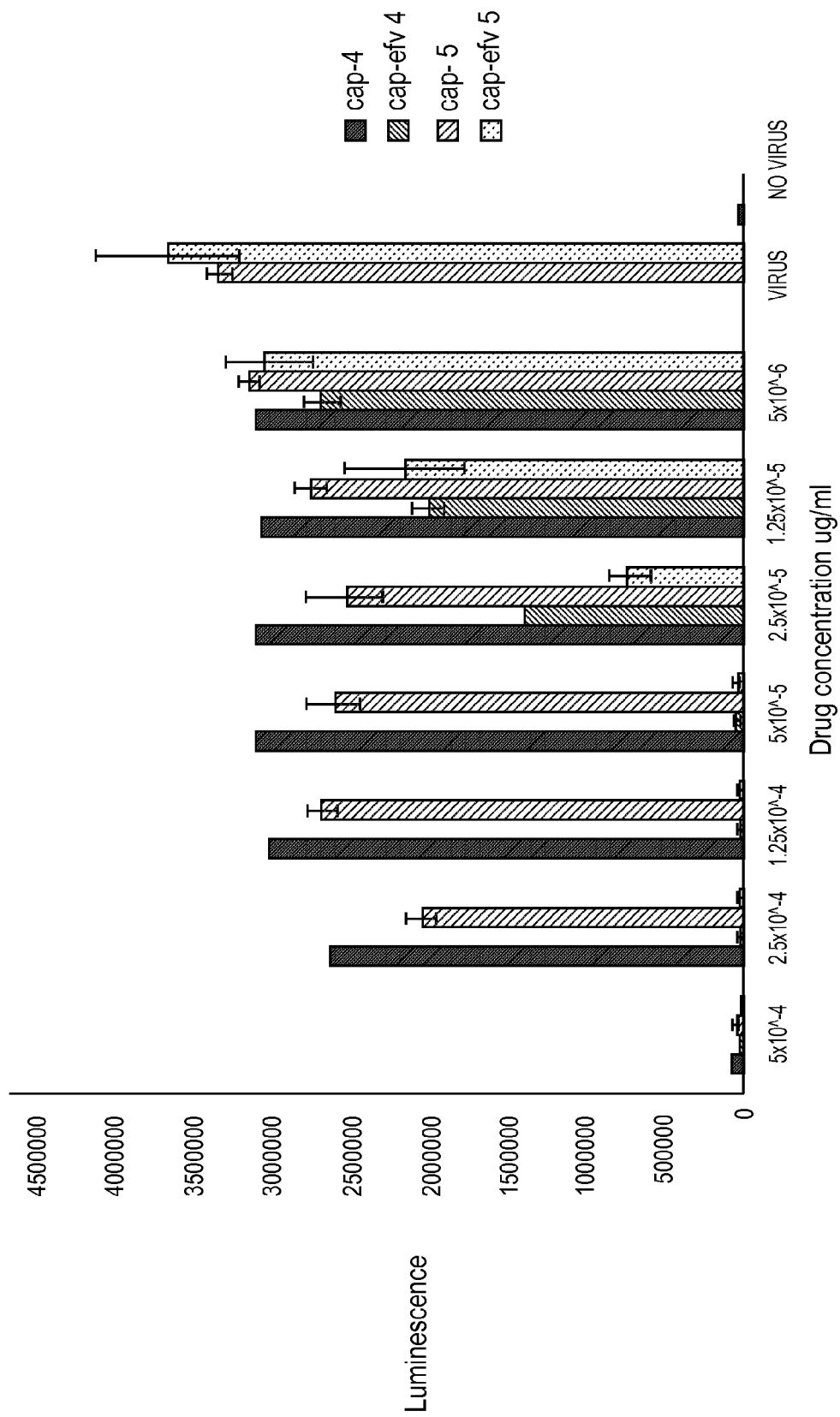
FIG. 13 shows graphs depicting anti-HIV activity of CAP-EFV-NP from batch 4 and 5. Briefly, TZM-bl cells were pretreated with either CAP-NP but no drug from bath 4 (cap-4) or batch 5 (cap-5), or CAP-NP loaded with EFV from batch 4 (cap-efv 4) or batch 5 (cap-efv 5), and then inoculated with HIV-$1_{NL4-3}$. After incubating the cells for a defined period of time, cells were lysed, a luciferase substrate was added, and luminescence was expressed as relative luminescence units.
Figure 14:
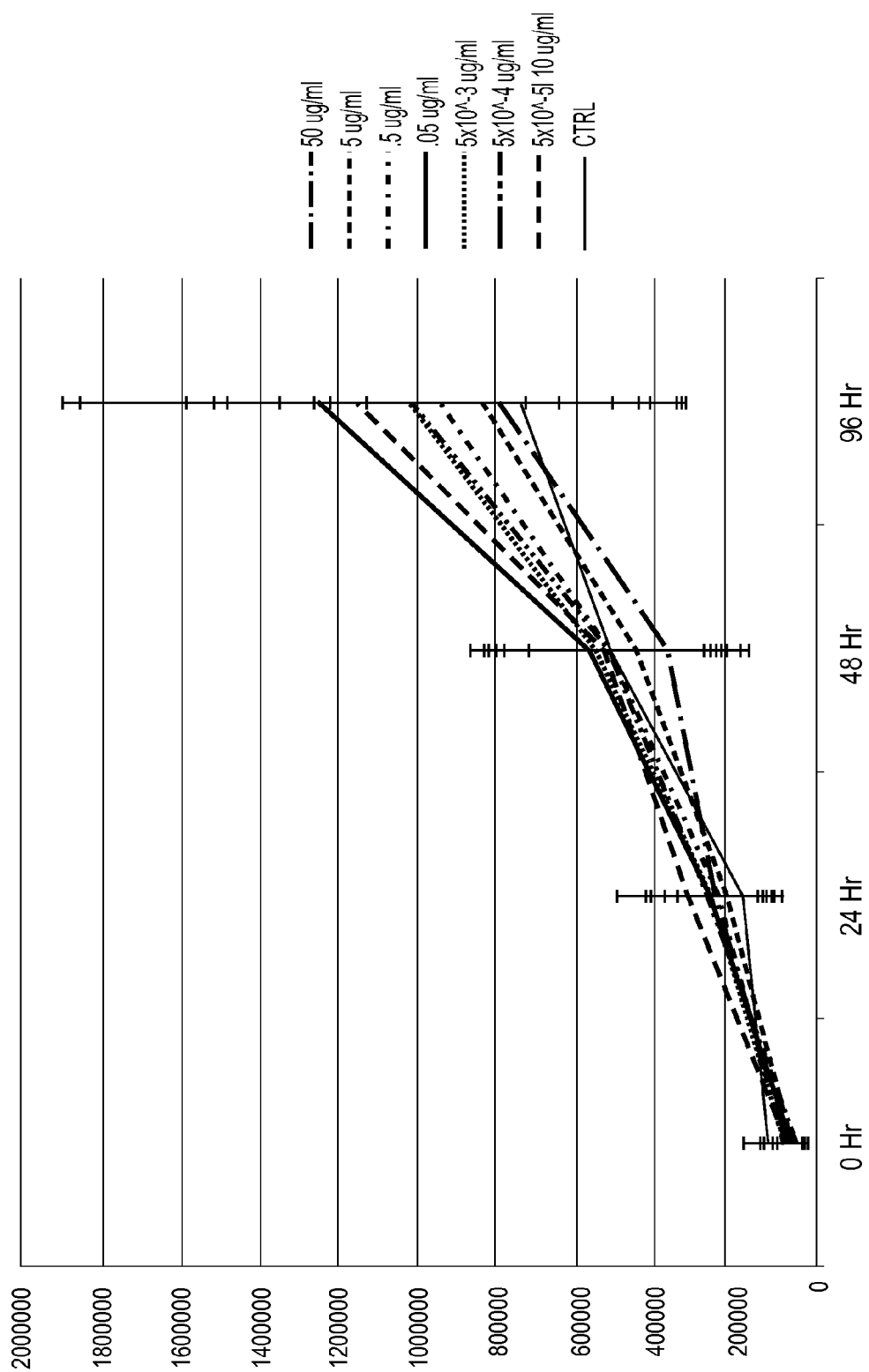
FIG. 14 shows a line graph depicting cytotoxicity of CAP-NP from batch 5 to HeLa cells over 96 hours in vitro. Relative luminescence is graphed on the y-axis, corresponding to HeLa cell viability.

Cytotoxicity of RAL-EFV-NPs, CAP-NPs, and CAP-EFV-NPs were tested against non-immune HeLa cells and immune H9 T cells. Results of cytotoxicity studies for RAL-EFV-NPs are shown in FIG. 2. RAL-EFV-NP and RAL-EFV solution were added to triplicate H9 and HeLa cells at the RAL+EFV concentrations of 50, 25, 15, 10, 5, 2.5, 1 µg/ml. The nanoparticle formulation and drug solution were incubated with cells for 24 and 48 h. The luminescence of the live cells was measured using a CellTiterGlo protocol and compared to luminescence of control cells (no treatment) to obtain the percent cell viability. The cell viability of RAL-EFV solution treated H9 cells was significantly lower (P<0.05) compared to RAL-EFV-NPs indicating a cellular protective effect of RAL-EFV-NP. The RAL-EFV solution and RAL-EFV-NP treated HeLa cells did not show a significant difference in the cell viability. The cell viability values are averaged from 3 independent experiments. Therefore, these experiments demonstrate a protective effect of the nanoparticle formulation compared to the same drugs given in vitro to cells in solution. Similar results were seen for CAP-NPs (FIGS. 11 and 14).

Example 3

Anti-HIV Activity

Figure 3:
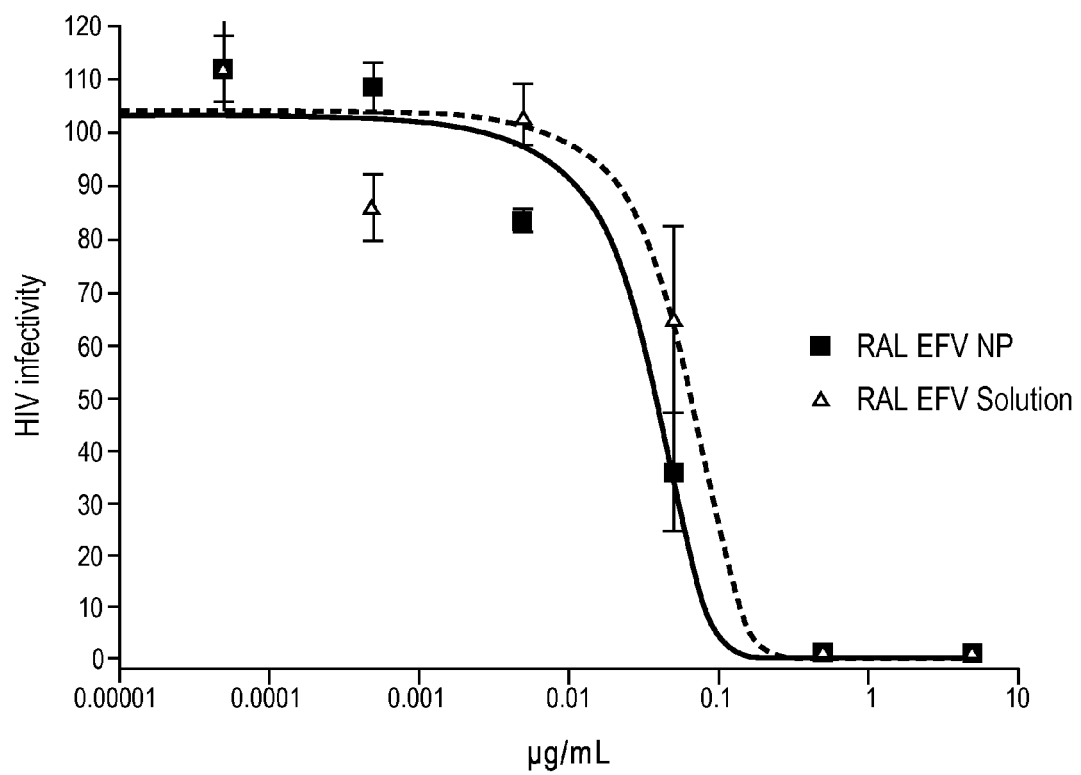
FIG. 3 plots the $IC_{90}$ curves for RAL-EFV solution and RAL-EFV-NP. RAL-EFV solution and RAL-EFV-NP were incubated with HIV-1 indicator TZM-bl cells at different concentrations starting for RAL+EFV concentration of 10 µg/ml.

The efficacy of RAL-EFV-NPs was compared to RAL-EFV solution by evaluating their $IC_{90}$ values against HIV-$1_{NL4-3}$ strain (FIG. 3). The inhibitory concentration for the RAL-EFV-NPs was significantly less (mean±SE, NP formulation 90.3±0.02, solution 144±0.067 ng/mL; P<0.05) than RAL-EFV solution. This indicates higher anti-viral activity of RAL-EFV-NPs most likely through enhanced intracellular drug delivery associated with the nanoparticle formulation. Anti-HIV activity was also seen for CAP-NPs and CAP-EFV-NPs (FIG. 9, 10, 13).

Example 4

Studies on Intracellular Release of RAL and EFV from PLGA Nanoparticles

Figure 4:
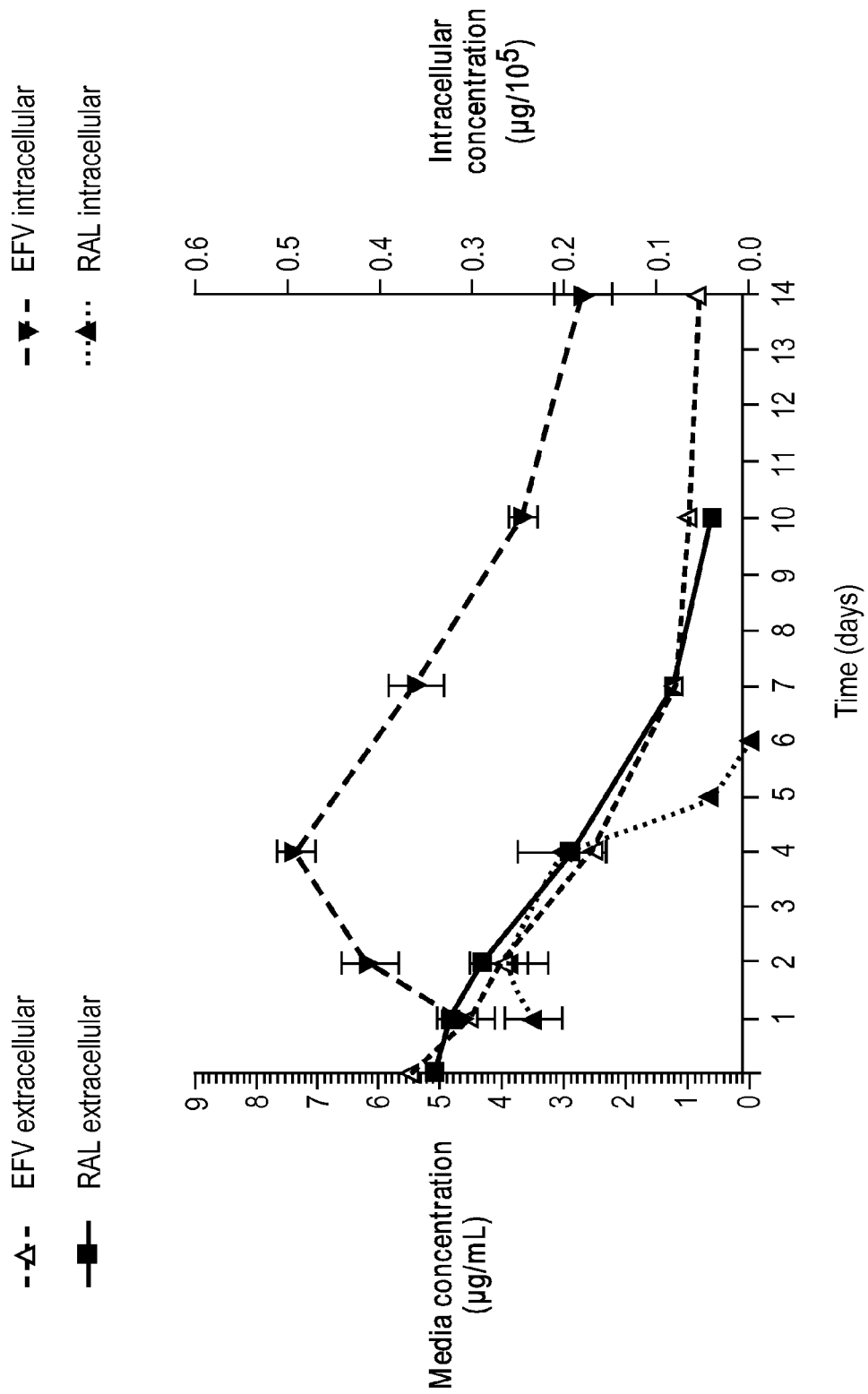
FIG. 4 graphically depicts the intracellular (HeLa cells) and extracellular (media) concentrations of RAL and EFV released from RAL-EFV-NP over a period of 14 days (n=6).

Intracellular and media concentrations of RAL and EFV released from RAL-EFV-NPs in HeLa cells are shown in FIG. 4. The nanoparticle formulation offered sustained intracellular release of raltegravir and efavirenz. Intracellular efavirenz concentrations were undetectable from efavirenz solution after 2 days in vitro. The intracellular concentration of EFV on day 14 was >150 ng/$10^5$ cells. The $IC_{90}$ in these experiments averaged 90.3 ng/mL and therefore the day 14 efavirenz concentration was above the $IC_{90}$ for the entire 14 days. Raltegravir intracellular concentration declined over the course of 6 days and was below the detectable limit of this assay on day 6. However, RAL was present in the media for 10 days, leading one to conclude that protection from HIV-1 infection could occur for 7 days with this combination product. Further experiments in vivo are necessary to confirm these results.

Example 5

Development of a Thermosensitive Vaginal Gel

Figure 5:
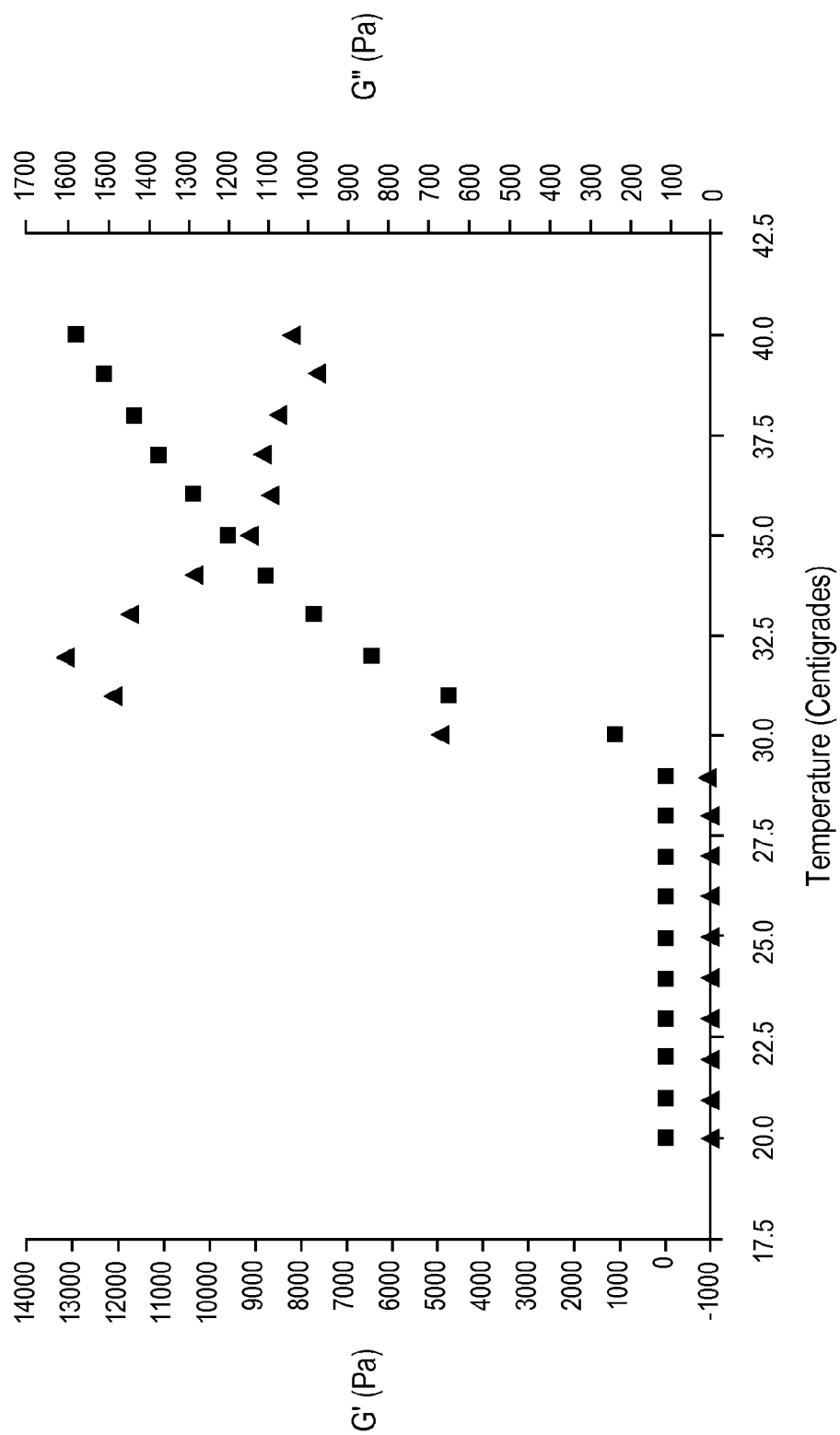
FIG. 5 depicts the sol-gel transition profile of thermosensitive gel (20% PLURONIC® F127 +1% PLURONIC® F68) demonstrating variations of the elastic (G'; lefty-axis) and viscous (G"; right y-axis) moduli, as a function of temperature. The elastic modulus increases after 30° C. indicating initiation of thermo gelation process and increases further with increase in the temperature indicating formation of firm gel at 37° C.
Figure 6:
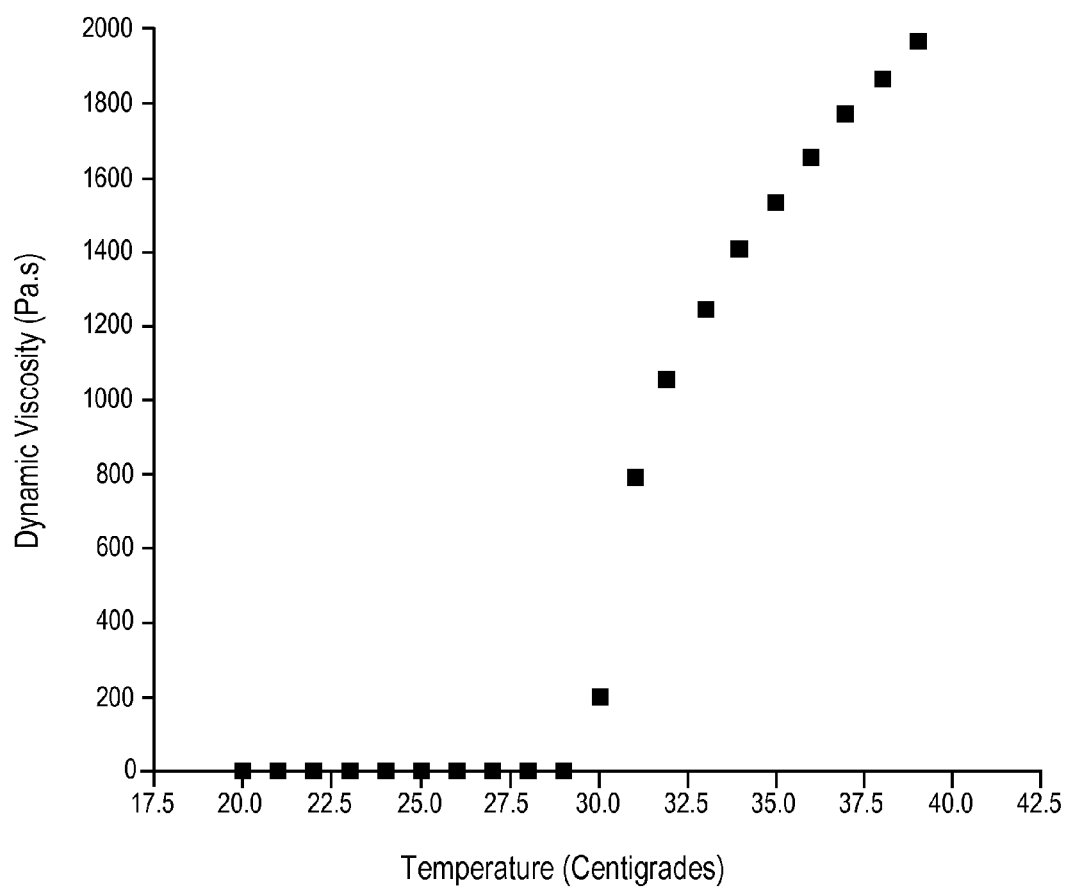
FIG. 6 graphically depicts the dynamic viscosity of the thermosensitive gel as a function of temperature. The viscosity of the thermosensitive gel starts increasing after 30° C. indicating initiation of thermogelation process and increases further with increase in the temperature.
Figure 7A:
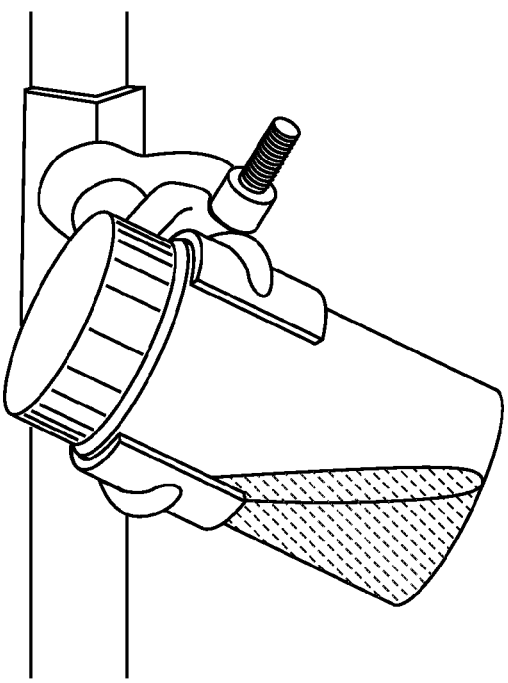
FIG. 7 shows images of the thermosensitive gel containing RAL-EFV-NP at room temperature (A) and at 37° C. (B).
Figure 7B:
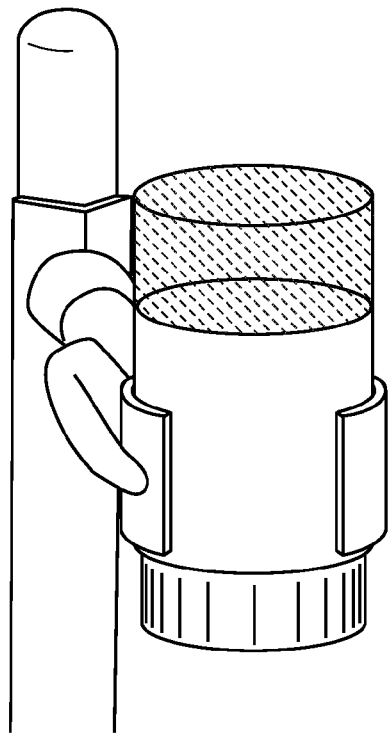

The present investigation was focused on developing thermosensitive gels to enable vaginal delivery of RAL-EFV-NP. Various compositions were studied to obtain a thermosensitive gel with optimal characteristics. The temperature of thermogelation obtained for various compositions is listed in Table 1 and Table 2 outlines the gel composition that was determined to be of use for further experiments. The addition of Pluronic F68 had considerable effect on the thermogelation of the PLURONIC® F127. PLURONIC® F127 (20%) and PLURONIC® F68 (1%) showed optimal thermogelation in this investigation. The sol-gel transition curves for this composition and effect of temperature on the viscosity obtained using rheometry are provided in FIGS. 5 and 6. FIG. 7 shows a photo of the RAL-EFV-NP gel before and after thermogelation.

TABLE 1

Various compositions tried for development of thermosensitive vaginal gel

| Composition Number | PLURONIC ® F127 (% w/v) | PLURONIC ® F68 (% w/v) | Thermogelation temperature |
|---|---|---|---|
| 1 | 20% | — | 27.5 ± 1° C. |
| 2 | 18% | 2% | >37° C. |
| 3 | 20% | 2% | >37° C. |
| 4 | 18% | 1% | >37° C. |
| 5 | 20% | 1% | 32.5 ± 1.5 |

TABLE 2

Composition of the RAL-EFV-NPs loaded thermosensitive gel

| Components | Quantity |
|---|---|
| PLURONIC ® F127 | 2 g (20% w/v) |
| PLURONIC ® F68 | 0.1 g (1% w/v) |
| DMSO | 0.15 ml (1.5% v/v) |
| N-methyl pyrrolidone | 0.1 ml (1% w/v) |
| RAL-EFV-NPs in citrate pH 4.5 buffer | 10 ml |

Example 6

Characterization of Nanoparticle Transfer from the Thermosensitive Gel using Transwells.

Figure 8A:
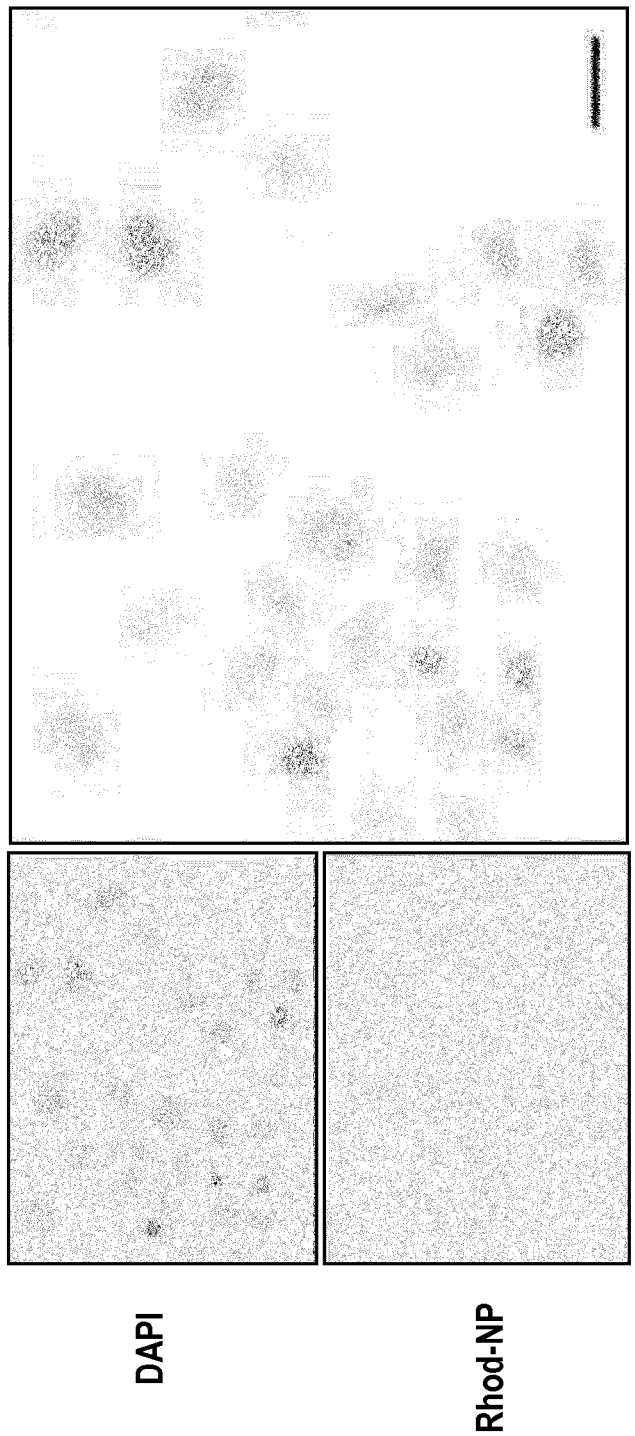
FIG. 8 shows fluorescent images of HeLa cells after 15 min (A) and 30 min (B) incubation with the thermosensitive gel containing rhodamine 6G labeled PLGA nanoparticles in the transwell.
Figure 8B:
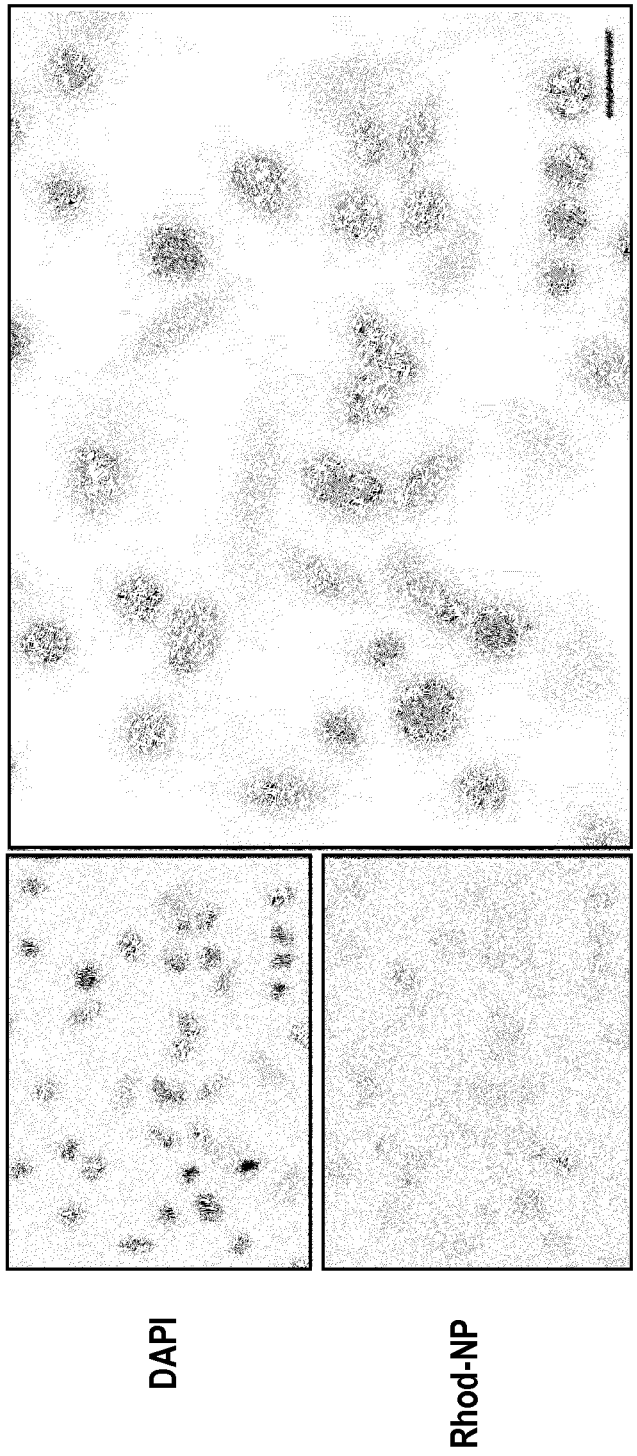
Figure 10:
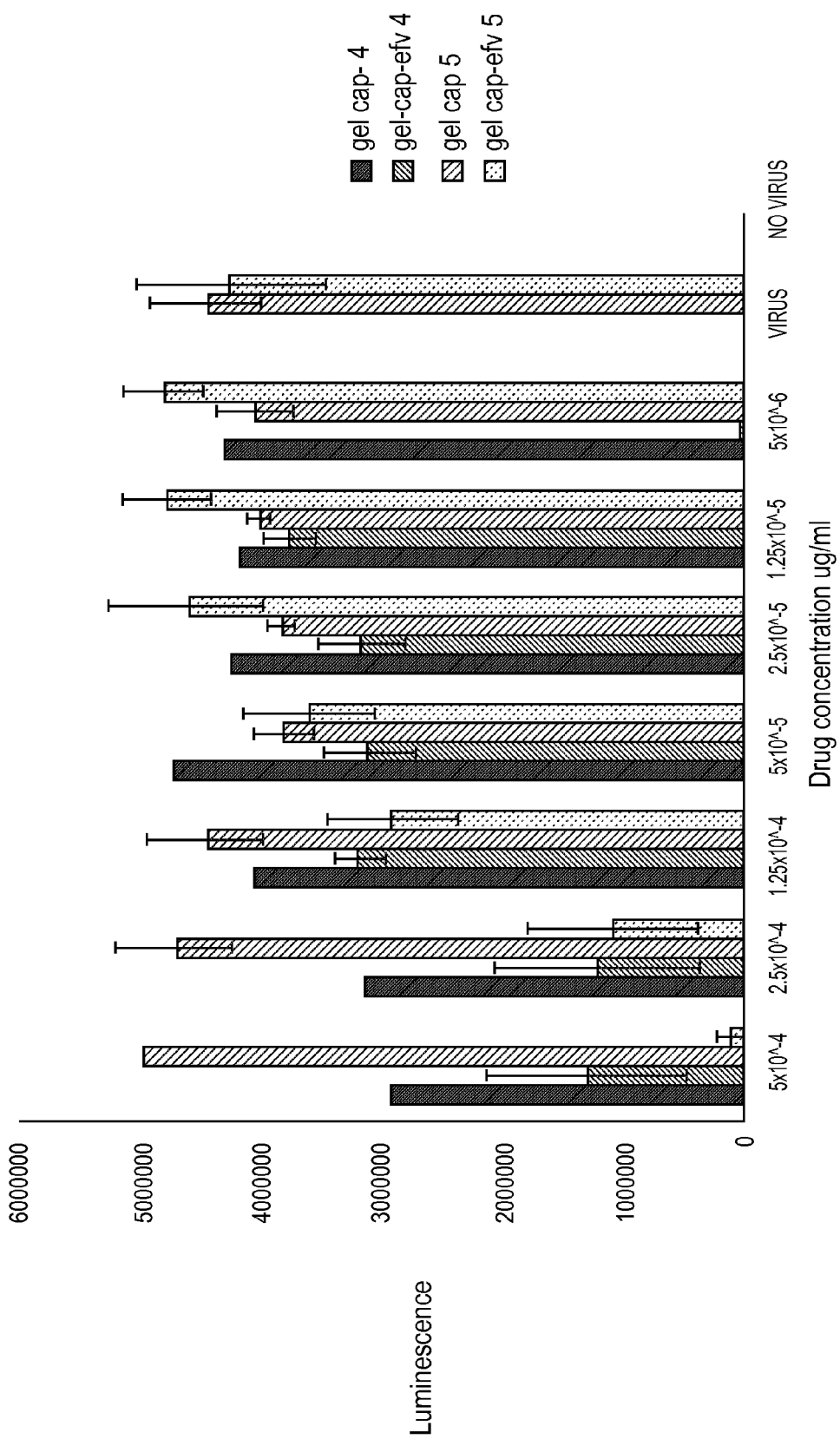
FIG. 10 shows graphs depicting anti-HIV activity of a thermosensitive gel containing CAP-NP or CAP-EFV-NP prepared from two different batches. Briefly, TZM-bl cells were pretreated with either gel containing CAP-NP from batch 4 (gel cap-4), gel containing CAP-EFV-NP from batch 4 (gel cap-efv 4), gel containing CAP-NP from batch 5 (gel cap-5), gel containing CAP-EFV-NP from batch 5 (gel cap-efv 5) and then inoculated with HIV-$1_{NL4-3}$. After incubating the cells for a defined period of time, cells were lysed, a luciferase substrate was added, and luminescence was expressed as relative luminescence units.
Figure 15A:
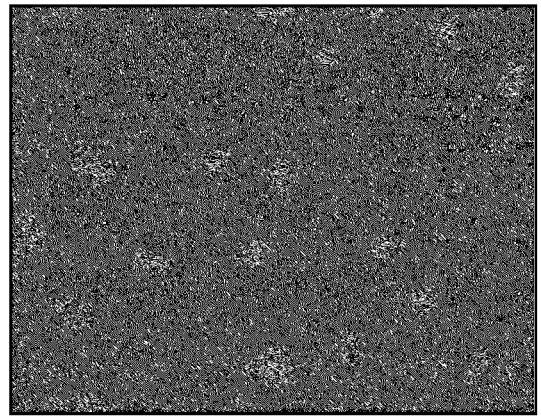
FIG. 15 shows fluorescent images of HeLa cells after 4 hr incubation with the thermosensitive gel containing rhodamine 6G labeled CAP nanoparticles in the transwell. Nuclei of HeLa cells are stained with DAPI (A); Rhodamine conjugated nanoparticles are imaged in (B); and (C) depicts a merged image (DAPI stained cells are blue, Rhodamine-conjugated nanoparticles are red).
Figure 15B:
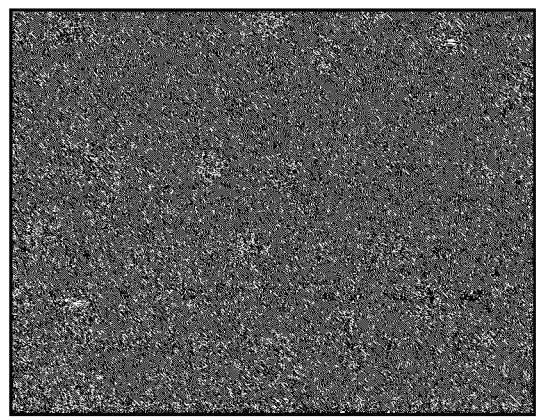
Figure 15C:
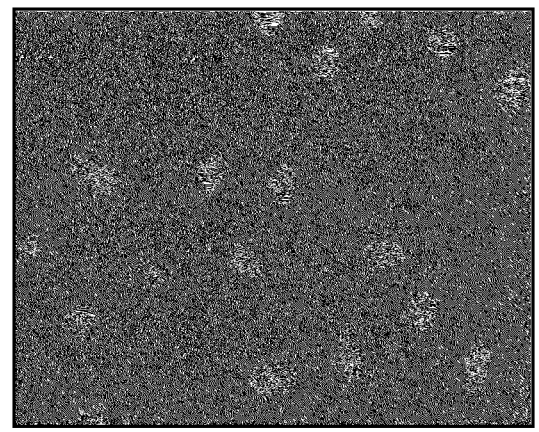
Figure 16A:
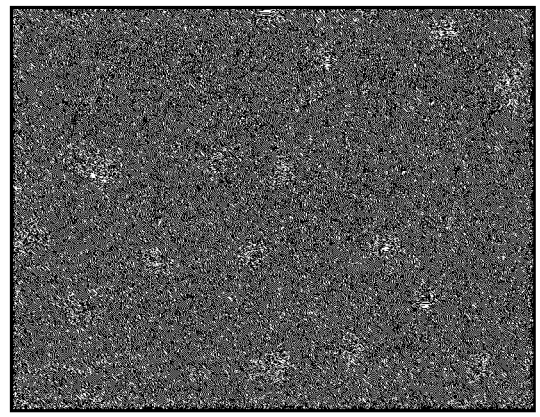
FIG. 16 shows fluorescent images of HeLa cells after 24 hr incubation with the thermosensitive gel containing rhodamine 6G labeled CAP nanoparticles in the transwell. Nuclei of HeLa cells are stained with DAPI (A); Rhodamine conjugated nanoparticles are imaged in (B); and (C) depicts a merged image (DAPI stained cells are blue, Rhodamine-conjugated nanoparticles are red).
Figure 16B:
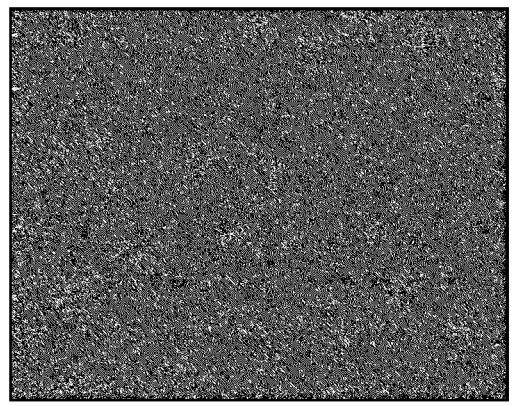
Figure 16C:
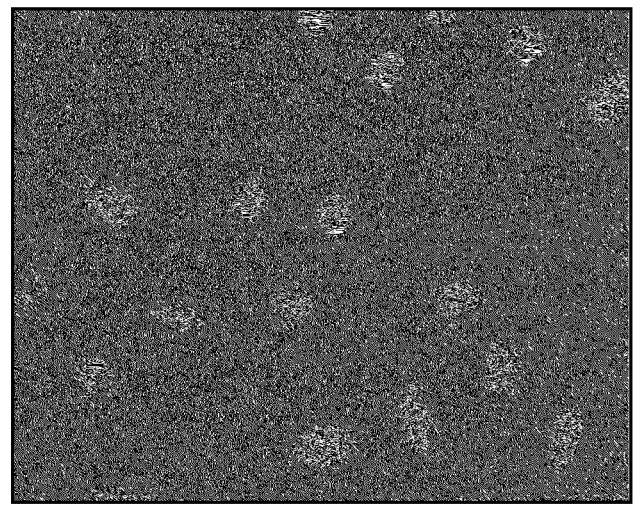

Experimentally, it was determined whether nanoparticles could be released from thermosensitive gel, move through a semi-permeable membrane and be taken up by HeLa cells. To perform these experiments, transwell experiments were utilized where the gel is placed on the top of the transwell support and the cells are adhered to the bottom of the culture well. Fluorescent nanoparticles fabricated similarly to the RAL-EFV NPs were used to determine the time before the nanoparticles transfer to the cells. The results of these experiments are shown in FIGS. 8 A and B. Fluorescent nanoparticles were able to transfer through transwell membrane and were taken up by HeLa cells within 30 min. Similar results were also seen with fluorescent nanoparticles fabricated similarly to the CAP-NPs (FIGS. 15 and 16).

Example 7

CAP-EFV-NP Preparation and Characterization

CAP and EFV (5 mg each) were dissolved in ethyl acetate (5-10 ml containing 50 mg PLGA polymer) and added in dropwise fashion to an aqueous solution of 2% PLURONIC® F127. Nanoparticles were produced by homogenization using a probe homogenizer. Homogenization occurred over 10-15 minutes at 80% power. The preparation was placed on a stir plate with magnetic stir bar to evaporate the organic solvent (usually over 4-12 h). The formulated nanoparticles were checked for size using light dynamic scattering, polydispersity, and surface charge. The nanoparticles were then used in the formulated gel, used for cytotoxicity experiments, or other in vitro experiments.

Discussion of Examples 1-7

The present investigation was focused on exploring the potential of polymeric nanoparticles for coital-independent vaginal prophylaxis of HIV. For successful vaginal delivery, the developed nanoparticles should preferably have small particle size and ability to rapidly penetrate through vaginal mucus in order to deliver the antiretroviral drug to the vaginal epithelium. These experiments show the successful development of sub-100 nm nanoparticles composed of PLGA, a FDA approved biodegradable polymer to deliver a combination of raltegravir and efavirenz (RAL-EFV-NPs). The PLURONIC® F127 was employed as a stabilizer for the development of RAL-EFV-NP. Research has shown rapid penetration of PLURONIC® F127 coated polystyrene nanoparticles through cervicovaginal mucus. Since, PLURONIC® F127 was employed for fabricating RAL-EFV-NPs, RAL-EFV-NPs can have mucus-penetrating ability. Fabricated RAL-EFV-NPs demonstrated different entrapment efficiency for raltegravir and efavirenz. This difference can be attributed to difference in their physicochemical properties. Raltegravir is a hydrophilic drug with negative log P value at pH 7.4 whereas efavirenz is a lipophilic drug with positive log P value. During emulsification of the organic phase of the nanoparticle fabrication process, some amount of raltegravir would partition into aqueous phase due to its hydrophilicity while efavirenz would reside mainly in the organic phase due to its higher lipophilicity resulting in increased association with hydrophobic PLGA as compared to raltegravir.

Osmolarity is an important criterion for development of successful vaginal formulations. The 1% tenofovir gel used in the CAPRISA-004 trial was hyperosmolar (3111 mOsm/kg) and resulted in epithelial stripping of polarized explants. Vaginal gels should have an osmolarity less than 1000 mOsm/kg to prevent mucosal irritation and damage to epithelial lining of the vagina (Friend 2010). Studies have shown that RAL-EFV-NPs had osmolarity less than 500 mOsm and are likely to be well tolerated compared to tenofovir 1% gel.

RAL-EFV-NPs and RAL-EFV solution showed cytotoxicity to HeLa and H9 cells at higher concentrations (25 and 50 µg/ml). Recently, studies have shown that EFV is toxic to the HeLa cells at the concentration higher than 25 µM. No cytotoxicity reports for H9 cells could be found. However, it is noteworthy that even though RAL-EFV-NPs showed toxicity at higher concentrations, the extent of cytotoxicity was significantly less than RAL-EFV solution (in H9 cells). This clearly demonstrated that nanoparticles can increase selectivity index of drugs. Similar observations have been reported for dapivirine loaded polycaprolactone nanoparticles (das Neves et al., 2012). On the other hand, HeLa cells did not show any significant difference in cytotoxicity caused by RAL-EFV-NPs and RAL-EFV solution. This difference could be due to difference in the sensitivity of H9 and HeLa cells towards drug treatment. The minimal cytotoxicity observed with RAL-EFV-NPs was due to encapsulation of raltegravir and efavirenz in the nanoparticles. This encapsulation minimizes interaction of free drug with cells. Furthermore, nanoparticles release these drugs in a sustained manner in the cellular milieu. Thus, cells are never exposed to high concentration of the antiretroviral drugs.

It should be noted that $IC_{50}$ experiments carried out in this investigation were adapted to establish the potential of RAL-EFV-NPs and RAL-EFV solution for prophylactic treatment. TZM-bl cells were treated with the RAL-EFV-NPs and RAL-EFV solution overnight, the media was removed, cells were washed, media was replaced with fresh media and the cells were infected with HIV after 24 h. Thus, cells would be infected with HIV-1 only if the treatment was unable to maintain effective concentrations. RAL-EFV-NPs were more active compared to the RAL-EFV solution. The lower $IC_{50}$ of the nanoparticle formulation could be due to ability of nanoparticles to transport and maintain higher concentrations of raltegravir and efavirenz inside the cells.

The difference in intracellular concentrations of raltegravir and efavirenz is likely due to differences in their half-lives and metabolic profiles. Raltegravir has a half life of 7-12 h (Iwamoto et al., 2008) whereas efavirenz has a half life of 40-55 h. Raltegravir is metabolized by uridine diphosphate glucuronosyltransferase (UGT1A1, UGT1A3 and UGT1A9) mediated glucuronidation. Efavirenz is primarily metabolized by cytochrome P450 (CYP2B6) mediated hydroxylation. It has been reported that HeLa cells express UGT1A1 and UGT1A9 whereas cytochrome P450 isoforms such as CYP3A4 are not present in HeLa cells. The absence of CYP2B6 mRNA in cervical epithelia has also been reported. In view of this, it can be assumed that HeLa cells can readily metabolize raltegravir released from the nanoparticles whereas efavirenz cannot get degraded intracellularly. This can explain the difference in the intracellular release of the raltegravir and efavirenz. The intracellular drug levels were focused on as this is the site of the drugs and HIV replication. However, the extracellular drug levels were also above the $IC_{90}$ for the virus.

Development of suitable vehicle to enable vaginal delivery of RAL-EFV-NPs is an important aspect for bench-to-bedside translation. In the present investigation, the development of thermosensitive gels for vaginal delivery of RAL-EFV-NPs was the focus. Thermosensitive gels are liquid at room temperature but form a firm gel at 37° C. once delivered inside the body. Thermosensitive gels are easy to handle and deliver as compared to conventional gels due to their liquid nature. However, it is important to develop a thermosensitive gel that can remain liquid even in sub-tropical and tropical countries or in the zone IV as classified by the ICH guidelines where average temperature is usually greater than 30° C. At the same time, thermogelation temperature should not be too close to 37° C. as body temperature shows variation as well. Thus, optimal thermogelation point of the gel was set to be between 30-33° C. for this investigation. PLURONIC® F127 (20%) and PLURONIC® F68 (1%) showed optimal thermogelation in this investigation and the RAL-EFV -NPs did not show any visible signs of aggregation after incorporation in gel.

Finally, transwell experiments were carried out to evaluate the transfer of the nanoparticles from the thermosensitive gel into the environment and cellular uptake. Interestingly, nanoparticles were phagocytosized by HeLa cells within 30 minutes indicating release of nanoparticles from gel and rapid uptake of released nanoparticles by HeLa cells.

Methods of Examples 1-7

(a) Materials

Poly-lactide-co-glycolide (A vg. Mol. Wt. 52000 Da, Inherent viscosity 0.59 dL/g in hexafluoroisopropanol) was purchased from Birmingham Polymers (Birmingham, AL). Raltegravir (RAL) and efavirenz (EFV) were purchased from Sequoia Research Ltd. (Pangboume, UK). Potassium dihydrogen phosphate (HPLC grade), acetonitrile (HPLC grade), dimethyl sulfoxide (DMSO, AR Grade), ethyl acetate (AR grade), citric acid (AR grade), trisodium citrate (AR grade), polyvinyl alcohol (88% hydrolyzed; Mol. Wt. 88000) and Rhodamine 6G were purchased from Fischer Scientific Ltd (Pittsburg, PA, USA). PLURONIC® F127, PLURONIC® F68 (BASF Corp., Edison, NJ, USA) and N-methylpyrrolidone (Pharmasolv®, Ashland Inc, Wayne, NJ, USA) were received as gift samples. Ultrapure water was used for all the experiments.

(b) Cell Culture

Human cervical (HeLa) cells and H9 cells were purchased from American Tissue Culture Collection (ATCC, Manassas, Va.). TZM-bl cells were procured through NIH AIDS Research and Reference Reagent Program. These indicator cells express luciferase under the control of the HIV-1 promoter. HeLa and TZM-bl cells were maintained in Dulbecco's Modified Eagle Media (DMEM, MediaTech Inc., Manassas, Va.) supplemented with 10% fetal bovine serum (FBS, Hyclone Inc., Utah), 4 mM L-glutamine, 100 U/mL penicillin and 100 µg/mL streptomycin (MP Biomedical Inc., Solon, Ohio) and maintained in a logarithmic growth phase. H9 cells were maintained in RPMI-1640 medium supplemented with 10% fetal bovine serum (FBS, Hyclone Inc., Utah), 4 mM L-glutamine, 100 U/mL penicillin and 100 µg/mL streptomycin (MP Biomedical Inc., Solon, Ohio). All cells were grown at 37° C. and 5% $CO_2$.

(c) Preparation of PLGA Nanoparticles Containing RAL and EFV Combination (RAL-EFV-NP)

Briefly, PLGA (50 mg) and PLURONIC® F127 (100 mg) were dissolved in 3 ml of ethyl acetate by heating at 40° C. in an incubating shaker bath. RAL (5 mg) and EFV (5 mg) were dissolved in a mixture of DMSO (0.15 ml) and N-methylpyrrolidone (0.1 ml) by heating at 40° C. in an incubating shaker bath. Ethyl acetate solution was added to the DMSO and N-methylpyrrolidone mixture containing RAL and EFV to obtain a homogenous solution (organic phase). The organic phase was emulsified in 10 ml of ultrapure water using a probe sonicator (UPIOOH; Hielscher USA, Inc., NJ, USA; Amplitude: 80% and Intensity: 0.8) for 15 min in an ice bath. The resultant oil-in-water emulsion was transferred to a 50 mL beaker and stirred at 700 rpm for 2 h using a magnetic stirrer to evaporate the ethyl acetate. Particle size, polydispersity index, and surface charge of resulting RAL-EFV-NPs were measured using dynamic light scattering (ZetaPlus instrument, Brookhaven Instruments Corp, NY, USA) as previously described (Shibata et al., 2012). All experiments were carried out in triplicate. RAL-EFV-NPs were sterile filtered through a 0.22 μm filter and used for further studies. For fabrication of fluorescent nanoparticles, Rhodamine 6G (1 mg) was dissolved in 3 mL ethyl acetate in place of antiretroviral drugs and processed as described above.

The entrapment efficiency was calculated by the following equation:

$$\% \ EE = \left(\frac{A_{initial} - A_{free}}{A_{initial}}\right) \times 100;$$

where $A_{\text{"initial"}}$ is the amount of drug/mL of nanoparticle dispersion and $A_{\text{"free"}}$ is amount of drug/mL of filtrate obtained by centrifugation of nanoparticles. Triplicate experiments were performed.

(d) Imaging of RAL-EFV-NPs by SEM

RAL-EFV-NPs were placed on the slide surface and allowed to dry. The slide was sputter coated with 2% w/v uranyl acetate, dried, and then visualized by using a JEOL-40A (JEOL Ltd, Sheboygan, Wis.) scanning electron microscope (Shibata et al., 2012).

(e) In vitro Cytotoxicity Studies

In vitro cytotoxicity of RAL-EFV-NPs and RAL-EFV solution was studied using H9 and HeLa cells. Triplicate sets of cells were seeded in 96-well plates at a density of 4000 cells/well in triplicate and allowed to attach to wells overnight. RAL-EFV-NP and RAL-EFV solution were added to obtain combined RAL and EFV concentration of 50, 25, 15, 10, 5, 2.5 and □1 μg/mL in each well. Cell viability was assessed after 48 h using the CellTiter Glo protocol (Promega, Madison, Wis.) according to the manufacturer's instructions. The luminescence obtained for different concentrations of RAL-EFV-NPs and RAL-EFV solution was compared to control cells (no treatment) to calculate % cell viability. The results of the cell viability were compared between the two drug groups using Student's T test. Experiments were performed in triplicate. Similar methods were used to study the in vitro cytotoxicity of CAP-EFV-NPs.

(f) Anti-HIV Activity

Activity of RAL-EFV-NPs and RAL-EFV solution against HIV-$1_{NL4-3}$ was determined using TZM-bl HIV-1 indicator cells as per reported method with suitable modifications (Fletcher et al., 2009). Briefly, TZM-bl cells were seeded in 24-well plates at a density of 2×10$^5$ cells per well. After 24 h, the cells were treated with six 10-fold dilutions of RAL+EFV loaded PLGA nanoparticles or RAL+EFV solution. After 24 h, media from all wells was vacuumed to remove RAL-EFV-NP or RAL+EFV solution and replaced with fresh media. On the following day, the cells were inoculated with HIV-$1_{NL4-3}$ virus (25 μL) for 4 h. The cells were washed and incubated for 48 h. Cells were washed with PBS, lysed with 150 μl M-PER solution (Thermo Scientific, Rockford, Ill.) and clarified by centrifugation. A luciferase substrate was added to the lysate and the resulting luminescence, expressed as relative luminescence units (RLU), was determined by the luminometer Instinct (Promega, Madison, Wis.). The results were normalized by comparing RLU of RAL+EFV treatment groups with that of the positive control (HIV infected cells without antiretroviral treatment) and data obtained was plotted to obtain an IC$_{50}$ concentration-response curve for RAL+EFV nanoparticles compared to RAL+EFV solution using GraphPad Prism software. All the experiments were performed in triplicate. Similar methods were used to study the anti-HIV activity of CAP-EFV-NPs.

(g) Studies on Intra-cellular Release of Raltegravir and Efavirenz from RAL-EFV-NP Intracellular release of RAL and EFV from RAL-EFV-NPs was studied using HeLa cells. HeLa cells (1×10$^5$ cells/well) were seeded onto 12-well plates and cultured overnight. RAL-EFV-NPs were added to wells with a combined starting raltegravir+efavirenz concentration of 10±2 μg/well. Release of RAL and EFV in HeLa cells and in culture media was analyzed by HPLC on day 1, 2, 4, 5, 6, 7, 10 and 14.

During the period of 14 days, half the amount of the cell culture media (0.5 mL) in all the wells was replaced with fresh media after every 2-3 days. On the day of analysis, all the media from triplicate wells was removed. Acetonitrile (0.5 mL) was added to the wells for cell lysis and extraction of RAL and EFV from the cells. The concentration of RAL and EFV in the culture medium and cell lysate was analyzed by HPLC. For analyzing concentration of RAL and EFV in the culture media, 0.5 mL of acetontrile was added to 0.5 mL of culture media and the mixture was vortexed for 1 minute, centrifuged at 14000 rpm for 15 min. The supernatant (20 μL) was injected in HPLC for analysis of RAL and EFV. A total of three experiments were performed. For analyzing RAL and EFV in the cell lysate, 100 μL of cell lysate was transferred in an microfuge tube and 20 μL of this solution was injected in HPLC.

A reverse phase-HPLC method was developed and validated for simultaneous determination of the RAL and EFV from various samples. The HPLC apparatus consisted of a pump (LC-10ATvp), system controller (SIL-10ADvp), degasser unit (DGU-14A), refrigerated auto-sampler (SIL-10ADvp), a UV-Vis detector (SPD-10ADvp) and a column heater (Shimadzu Corporation, Columbia, Md.). Samples were run through a C18 pre-column and a Gemini C18 reverse-phase column [150×4.5 mm (I.D.)] with 5 μm particle size packing (Phenomenex, Torrance, Calif.). The mobile phase consisted of acetonitrile and 25 mM KH$_2$PO$_4$ solution (55:45). For HPLC analysis, the flow rate of the mobile phase was at 0.9 mL/min, column oven was set at 35° C., injection volume was 20 μL and the dual wavelength detector was set at 212 nm (for EFV) and 300 nm (for RAL). The retention time for the RAL was 3.25 min and for EFV was 10.4 min. For standard curve, RAL and EFV stock solutions (1 mg/mL) were prepared in water and acetonitrile respectively. The stock solutions were diluted with acetonitrile to obtain solutions of various concentrations. Standard curve was obtained by injecting 1-10 μg/mL of RAL and EFV. All the experiments were performed in triplicate. The inter-day and intra-day variability for the standard curve was always <10%.

(h) Development of a Thermosensitive Vaginal Gel

For development of a thermosensitive vaginal gel, RAL-EFV-NPs or CAP-EFV-NP were prepared in pH 4.5 aqueous citrate buffer. A known quantity of Pluronics was added to the nanoparticle dispersion (5 mL) and the dispersions were stored overnight in the refrigerator to dissolve Pluronics. On the next day, the dispersions were gently stirred to obtain a homogenous translucent solution. The thermogelation point of the gel and dynamic viscosity were determined using a AR2000 rheometer (TA Instruments, Delaware, USA). A stainless steel cone/plate geometry (diameter: 40 mm, angle: 20 and gap: 50 μm) was used for the measurements. For measuring thermogelation temperature, the gel was subjected to various temperatures starting from 20° C. to 40° C. under a constant oscillatory frequency (1 Hz) and % strain (0.1). The elastic (or storage) modulus G' and the viscous (or loss) modulus G" were obtained from a phase angle and were plotted as a function of temperature using Rheology Advantage data analysis software. All the experiments were performed in triplicate.

(i) Characterization of Transfer of Fluorescent PLGA Nanoparticles from Thermosensitive Gel Using Transwells HeLa cells were plated at $0.5 \times 10^6$ cells/ml on Poly-D Lysine precoated 12 mm BD BioCoat* coverslips (BD Biosciences, San Jose, Calif.). Cells were cultured overnight in DMEM plus 10% fetal calf serum at 37° C., 5% $CO_2$. Thermosensitive gel (100 µl) containing Rhodamine 6G labeled fluorescent PLGA nanoparticles was placed on 0.4 µm transwell permeable supports (Corning Inc. Life Sci., MA, USA) at 37° C. for 10 min to allow gel solidification. Transwells were placed above HeLa cells for 15, 30 min, 2 h, 12 h and 24 h. At each time point, duplicate transwells were removed and cells were fixed by adding 100 µL of 37% formaldehyde in culture media for 15 min at 37° C. Fixed cells were rinsed in 1×PBS and incubated with 300 ng/ml of DAPI for 15 min in 1×PBS. Cells were rinsed three times in 1×PBS, mounted in Permount (Fisher) and viewed with 40×/63× objective on a Leica DMIL inverted fluorescent microscope. The images were captured without software enhancement. Similar methods were used to study the activity of fluorescent CAP nanoparticles.

(j) Statistical Analysis

Results are reported as mean±SEM for all experiments. Statistical significance was evaluated using Student's t-test or analysis of variance (ANOVA, GraphPad Prism). Differences were considered statistically significant at $p<0.05$.

What is claimed is:

1. An antiretroviral composition that can be administered prophylactically up to and including seven days prior to exposure to the retrovirus, the composition comprising:
    a mixture of thermosensitive polymers comprising poloxamers including Poloxamers 188 and Poloxamers 407, wherein the ratio of Poloxamers 407 (% weight/volume) to Poloxamer 188 (% weight/volume) in the mixture is about 20:1, and
    a nanoparticle comprising a biodegradable polymer and at least one antiretroviral drug,
    wherein the composition is a solution at room temperature and is a gel at a temperature between 30° C. and 33° C.

2. The composition of claim 1, wherein the biodegradable polymer is selected from the group consisting of polylactide-co-glycolide, polycaprolactone, cellulose acetate phthalate, or a combination thereof.

3. The composition of claim 1, wherein the antiretroviral drug is encapsulated within the nanoparticle, directly conjugated to the nanoparticle, indirectly conjugated to the nanoparticle, or a combination thereof.

4. The composition of claim 3, wherein the antiretroviral drug has a negative log P value at pH 7.4.

5. The composition of claim 3, wherein the antiretroviral drug has a positive log P value at pH 7.4.

6. The composition of claim 3, wherein the antiretroviral drug is selected from a group consisting of raltegravir, efavirenz, cellulose acetate phthalate, tenofovir, emtricitabine, and a combination thereof.

* * * * *